(12) United States Patent
Weir et al.

(10) Patent No.: US 10,033,027 B2
(45) Date of Patent: Jul. 24, 2018

(54) PULL TAB ASSEMBLIES FOR TRANSITIONALLY INTERRUPTING AN ELECTRICAL CONNECTION WITH A BATTERY

(71) Applicant: Merit Medical Systems, Inc., South Jordan, UT (US)

(72) Inventors: Steven Weir, Sandy, UT (US); Blaine Johnson, Riverton, UT (US); Gregg B. Stanger, Centerville, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 272 days.

(21) Appl. No.: 15/059,545

(22) Filed: Mar. 3, 2016

(65) Prior Publication Data

US 2016/0260958 A1    Sep. 8, 2016

Related U.S. Application Data

(60) Provisional application No. 62/128,029, filed on Mar. 4, 2015.

(51) Int. Cl.
*H01M 2/34* (2006.01)
*A61M 5/00* (2006.01)
*H01M 2/10* (2006.01)
*H01M 10/42* (2006.01)

(52) U.S. Cl.
CPC ............... *H01M 2/34* (2013.01); *A61M 5/00* (2013.01); *H01M 2/1022* (2013.01); *H01M 2/1044* (2013.01); *H01M 10/425* (2013.01)

(58) Field of Classification Search
CPC ........... H01M 2/06; H01M 2/34; H02J 7/0045
See application file for complete search history.

(56) References Cited

U.S. PATENT DOCUMENTS

| D309,663 S | 7/1990 | Robinson |
| D330,078 S | 10/1992 | Porter |
| D330,763 S | 11/1992 | Penny |
| D331,107 S | 11/1992 | Kanner |
| 5,215,523 A | 6/1993 | Williams et al. |

(Continued)

FOREIGN PATENT DOCUMENTS

| WO | 2011097487 | 8/2011 |
| WO | 2011119896 | 9/2011 |
| WO | 2015020895 | 2/2015 |

OTHER PUBLICATIONS

European Search Report dated Mar. 15, 2017 for EP148341993.

(Continued)

*Primary Examiner* — Imran Akram
(74) *Attorney, Agent, or Firm* — Stoel Rives LLP

(57) ABSTRACT

Pull tab assemblies and related components and methods are disclosed herein. Some pull tab assemblies are configured to selectively interrupt and reestablish connections between a battery and a battery contact of an electronic circuit. Some pull tab assemblies include perforated pull tabs and/or pull tabs in which a proximal portion of the pull tab is configured to be cut or removed. Some pull tabs are designed to remain within a slot of the housing to impede fluid entry into the housing. Some methods disclosed herein involve programming memory that is disposed within a housing of a pull tab assembly or device.

14 Claims, 14 Drawing Sheets

(56) References Cited

U.S. PATENT DOCUMENTS

| | | |
|---|---|---|
| 5,259,838 A | 11/1993 | Taylor et al. |
| 5,318,533 A | 6/1994 | Adams et al. |
| 5,383,855 A | 1/1995 | Nicholson et al. |
| 5,387,194 A | 2/1995 | Williams et al. |
| 5,449,345 A | 9/1995 | Taylor et al. |
| 5,453,091 A | 9/1995 | Taylor et al. |
| 5,562,621 A | 10/1996 | Claude et al. |
| 5,647,847 A | 7/1997 | Lafontaine et al. |
| 5,695,466 A | 12/1997 | Lopez et al. |
| 6,139,523 A | 10/2000 | Taylor et al. |
| D439,584 S | 3/2001 | Wang |
| D440,575 S | 4/2001 | Wang |
| 6,377,848 B1 | 4/2002 | Garde et al. |
| 6,389,143 B1 | 5/2002 | Leedom et al. |
| 6,394,977 B1 | 5/2002 | Taylor et al. |
| D523,871 S | 6/2006 | Hally |
| D524,321 S | 7/2006 | Hally |
| D525,984 S | 8/2006 | Hally |
| D528,124 S | 9/2006 | Hally |
| D528,559 S | 9/2006 | Hally |
| D534,916 S | 1/2007 | Hone |
| D537,449 S | 2/2007 | Hoefnagels |
| D550,691 S | 9/2007 | Hally |
| 7,351,223 B2 | 4/2008 | Call |
| D601,156 S | 9/2009 | Motohashi |
| D606,085 S | 12/2009 | Agnetta |
| D627,365 S | 11/2010 | Brinda |
| 7,892,202 B2 | 2/2011 | Lampropoulos et al. |
| D676,060 S | 2/2013 | Frost |
| D687,058 S | 7/2013 | Corcoran |
| D690,318 S | 9/2013 | Kluttz |
| D690,322 S | 9/2013 | Matas |
| D693,463 S | 11/2013 | Burger |
| D696,677 S | 12/2013 | Corcoran |
| D697,204 S | 1/2014 | Maier |
| D697,519 S | 1/2014 | Thomsen |
| D701,226 S | 3/2014 | Jung |
| D701,869 S | 4/2014 | Matas |
| D702,723 S | 4/2014 | Abratowski |
| D709,913 S | 7/2014 | Hurd |
| D714,931 S | 10/2014 | Sealfon |
| D720,449 S | 12/2014 | Galbraith |
| 8,915,891 B2 | 12/2014 | Bornhoft |
| D722,082 S | 2/2015 | Roberts |
| D727,354 S | 4/2015 | Park |
| D727,495 S | 4/2015 | Bown |
| 9,003,816 B2 | 4/2015 | Stefanski |
| D732,566 S | 6/2015 | Mitchell |
| 9,058,696 B2 | 6/2015 | Omiya |
| D740,300 S | 10/2015 | Lee |
| D741,356 S | 10/2015 | Park |
| D742,898 S | 11/2015 | Matas |
| D745,661 S | 12/2015 | Collins |
| D748,126 S | 1/2016 | Sarukkai |
| D749,092 S | 2/2016 | Lee |
| D749,206 S | 2/2016 | Johnson |
| 9,555,693 B2 | 1/2017 | Hopf et al. |
| 2001/0023490 A1 | 9/2001 | Gloecker et al. |
| 2004/0122369 A1 | 6/2004 | Schriver et al. |
| 2004/0176984 A1 | 9/2004 | White et al. |
| 2004/0260238 A1 | 12/2004 | Call |
| 2005/0148869 A1 | 7/2005 | Masuda |
| 2006/0282062 A1 | 12/2006 | Ishikawa et al. |
| 2007/0112299 A1 | 5/2007 | Smit et al. |
| 2007/0136679 A1 | 6/2007 | Yang |
| 2007/0156595 A1 | 7/2007 | Balassanian |
| 2007/0266344 A1 | 11/2007 | Olcott |
| 2008/0086087 A1 | 4/2008 | Spohn et al. |
| 2010/0217188 A1 | 8/2010 | Lampropoulos et al. |
| 2010/0274180 A1 | 10/2010 | Donovan et al. |
| 2011/0238082 A1 | 9/2011 | Wenderow et al. |
| 2012/0107670 A1* | 5/2012 | Viavattine .............. A61N 1/378 429/153 |
| 2012/0116366 A1 | 5/2012 | Houser et al. |
| 2013/0132028 A1 | 5/2013 | Crankson |
| 2013/0132887 A1 | 5/2013 | Amin |
| 2013/0157104 A1* | 6/2013 | Ulicny .................... H01M 2/34 429/121 |
| 2013/0197679 A1 | 8/2013 | Balakrishnan |
| 2013/0324989 A1 | 12/2013 | Leung |
| 2013/0331634 A1 | 12/2013 | Kaintz et al. |
| 2014/0045010 A1 | 2/2014 | Myers et al. |
| 2014/0275935 A1 | 9/2014 | Walsh et al. |
| 2015/0038901 A1 | 2/2015 | Lampropoulos et al. |
| 2015/0141915 A1 | 5/2015 | Lampropoulos et al. |
| 2015/0193553 A1 | 7/2015 | Petersen |

OTHER PUBLICATIONS

International Search Report and Written Opinion dated Jun. 14, 2016 for PCT/US2016/020574.

International Search Report and Written Opinion dated May 12, 2016 for PCT/US2016014822.

International Search Report and Written Opinion dated Nov. 11, 2014 for PCT/US2014/049364.

Notice of Allowance dated Jan. 21, 2016 for U.S. Appl. No. 29/504,961.

Notice of Allowance dated Mar. 18, 2016 for U.S. Appl. No. 29/504,954.

Notice of Allowance dated Apr. 13, 2016 for U.S. Appl. No. 29/504,954.

Notice of Allowance dated Jun. 27, 2016 for U.S. Appl. No. 29/504,937.

Office Action dated Feb. 23, 2016 for U.S. Appl. No. 29/504,937.
Office Action dated Feb. 13, 2018 for U.S. Appl. No. 14/449,506.
Office Action dated Sep. 25, 2017 for U.S. Appl. No. 14/608,904.
Office Action dated Sep. 26, 2017 for U.S. Appl. No. 14/449,506.

* cited by examiner

PULL TAB ASSEMBLIES FOR TRANSITIONALLY INTERRUPTING AN ELECTRICAL CONNECTION WITH A BATTERY

RELATED APPLICATIONS

This application claims priority to U.S. Provisional Application No. 62/128,029, filed on Mar. 4, 2015 and titled, "Pull Tab Assemblies and Related Methods," which is hereby incorporated by reference in its entirety.

TECHNICAL FIELD

The present disclosure relates generally to the field of pull tab assemblies, such as pull tab assemblies that are configured to selectively interrupt and establish a connection between a battery and a battery contact of an electronic circuit. The present disclosure also relates to methods of assembling and operating pull tab assemblies. In certain embodiments, pull tab assemblies include or are used in connection with medical devices, such as inflation devices.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

DETAILED DESCRIPTION

Figure 1A:
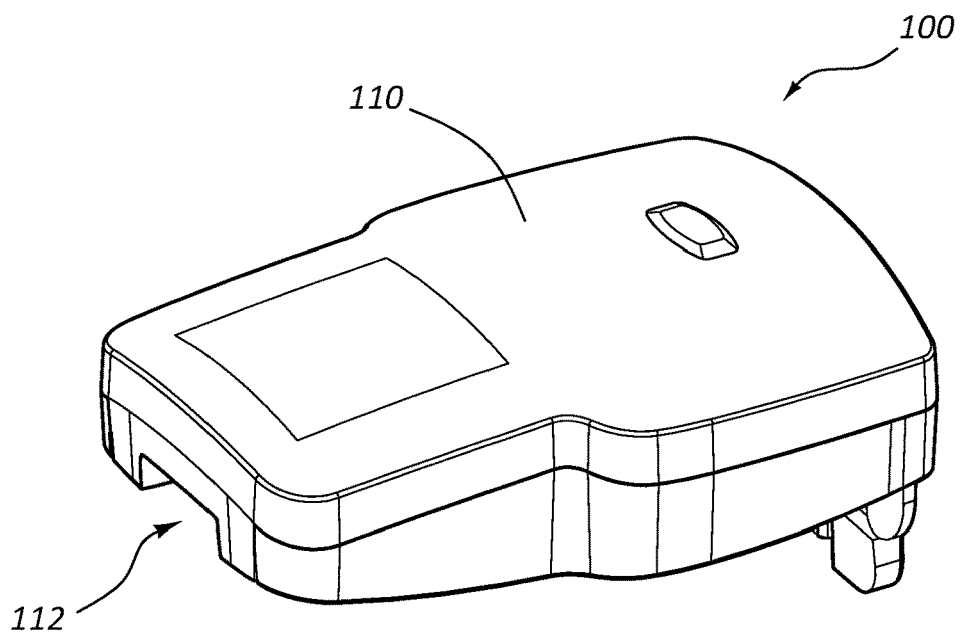
FIG. 1A is a perspective view of an assembly configured for use with a pull tab.

Pull tab assemblies, assemblies configured for use with a pull tab, and related components and methods are disclosed herein. Pull tab assemblies may include a battery, a first battery contact, and a pull tab. In some embodiments, the pull tab assemblies are configured to both establish and interrupt an electrical connection between a battery and a first battery contact. For example, in some embodiments, the pull tab assembly transitions from a state in which a battery is in electrical contact with a first battery contact to a state in which the battery is not in electrical contact with the first battery contact. Such a transition may arise from displacement of a pull tab relative to the battery and the first battery contact. In some embodiments, the pull tab assembly is configured to subsequently transition from a state in which the battery is not in contact with the first battery contact to a state in which the battery is in electrical contact with the first battery contact. In some embodiments, a pull tab assembly may transition from a state in which the battery is in electrical contact with a first battery contact to a state in which the battery is not in contact with the first battery contact by cutting or removing a proximal portion of the pull tab. In some embodiments, the pull tab may be configured to impede fluid entry through a slot in a housing. In some embodiments, the pull tab assembly includes an aperture that is configured to permit electrical contact between a battery and a first battery contact through the aperture.

Methods of assembling a device for selectively interrupting an electrical connection, or manipulating such a device, are also disclosed herein. Such methods may, inter alia, include the steps of (1) substantially enclosing a memory, a battery, and a battery contact within a housing and (2) programming the memory while the memory is enclosed within the housing.

Methods of interrupting and reestablishing an electrical connection between a battery and a battery contact are also disclosed herein. Such methods may include the steps of (1) cutting or removing a proximal portion of a pull tab and (2) displacing the pull tab.

The pull tab assemblies, devices, and related methods disclosed herein may include or be used in connection with other items or components. For example, pull tab assemblies may include or be used in connection with one or more medical instruments, such as inflation devices.

It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

The phrase "coupled to" refers to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component. With regard to wireless transfer of data between components which are wirelessly connected, coupled, or in communication with each other, any form of wireless interaction, including radio communication, optical communication, Bluetooth communication, Wi-Fi communication, infrared communication, sound wave transfer, and so forth are all within the scope of this disclosure. The term "transmitter" is broad enough to encompass devices that function as a transmitter, a receiver, or both (i.e., a transceiver).

The directional terms "distal" and "proximal" are given their ordinary meaning in the art. That is, the distal end of an assembly, a pull tab, or a medical device means the end of the assembly, pull tab, or medical device that is furthest from the practitioner during normal use. The proximal end refers to the opposite end, or the end nearest the practitioner during normal use. "Fluid" is used in its broadest sense, to refer to any fluid, including both liquids and gases. A pull tab assembly is in an "inoperable state" if a battery of the pull tab assembly is electrically disconnected from a battery contact due to the position of a pull tab. Conversely, a pull tab assembly is in an "operable state" if each of the anode and cathode of a battery of the pull tab assembly are electrically connected to battery contacts of an electronic circuit.

Figure 1B:
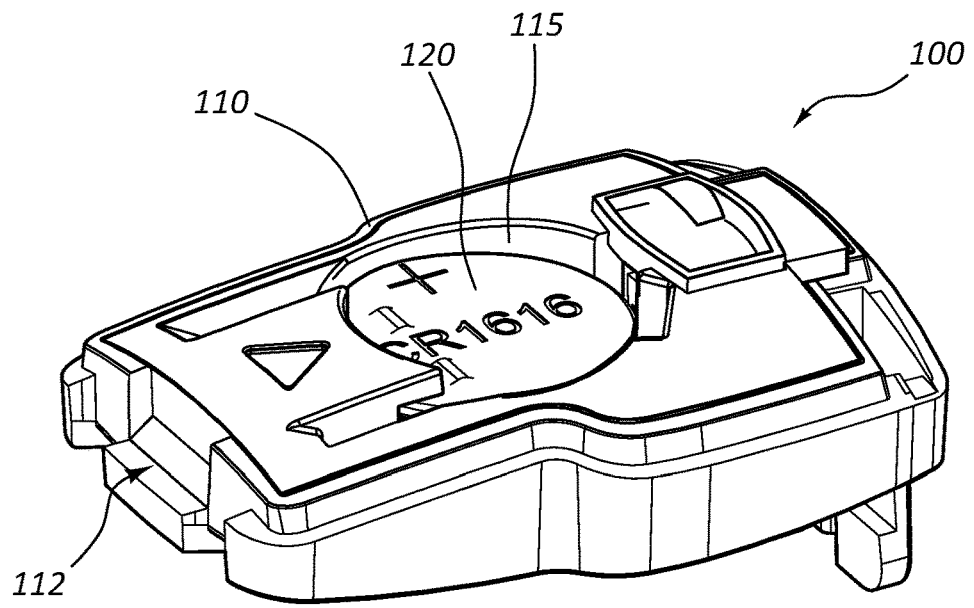
FIG. 1B is a perspective view of a first portion of the assembly of FIG. 1A.
Figure 1C:
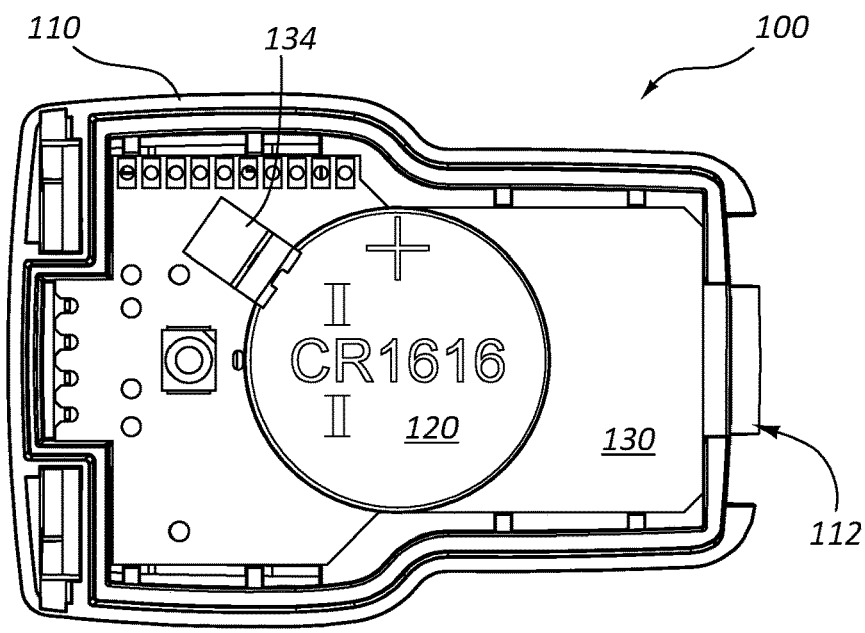
FIG. 1C is a top view of a second portion of the assembly of FIG. 1A.
Figure 1D:
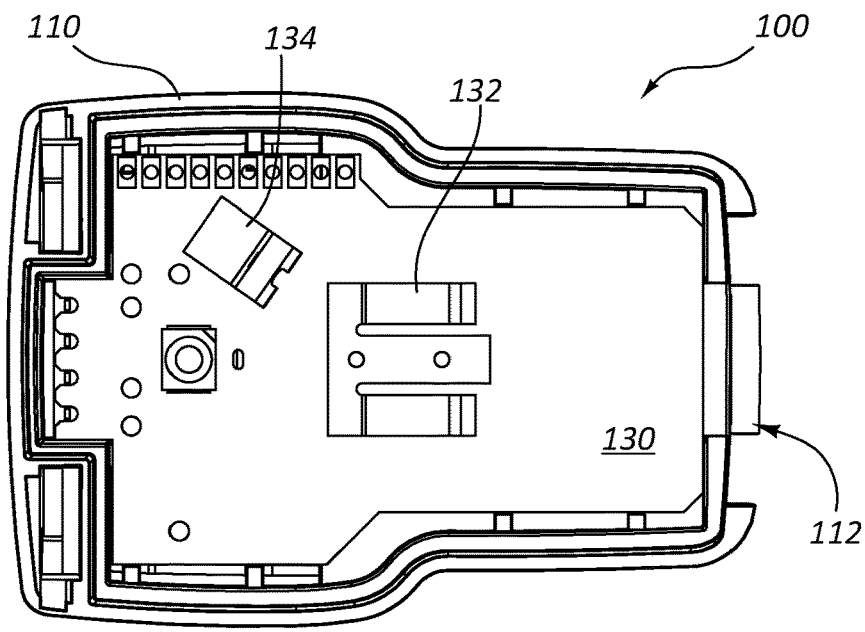
FIG. 1D is a top view of a third portion of the assembly of FIG. 1A.

FIGS. 1A-1D depict an assembly 100 configured for use with a pull tab. More particularly, FIG. 1A provides a perspective view of the assembly 100. FIG. 1B provides a perspective view of the assembly 100 in which a cover of the housing 110 is omitted to expose a battery holder 115. FIG. 1C provides a top view of a portion of the assembly 100 in which both the cover of the housing 110 and the battery holder 115 are omitted. And FIG. 1D provides a top view of another portion of the assembly 100, in which the cover of the housing 110, the battery holder 115 and a battery 120 are omitted, thereby exposing a battery contact 132.

With reference to FIGS. 1A-1D, the depicted assembly 100 includes a housing 110, a battery 120, and a circuit board 130. In the depicted embodiment, the housing 110 substantially encloses the battery 120 and the circuit board 130. The housing 110 may be formed from any suitable material or combination of materials. The housing 110 may protect the battery 120, the circuit board 130, and/or other components from environmental conditions (e.g., liquids, particulate matter, extreme temperatures, etc.) that may negatively affect the performance of components disposed therein. The housing 110 also includes a slot 112 through which a pull tab (not shown) may be at least partially withdrawn. As will be discussed in greater detail in connection with further embodiments, a pull tab may be used to selectively interrupt an electrical connection between the battery 120 and other components, such as a battery contact 132 of the circuit board 130.

The circuit board 130 includes at least one electronic circuit that is configured to electrically connect to opposite terminals of a battery 120. In some embodiments and circumstances, the electronic circuit is closed when in contact with opposing terminals of the battery 120, while in other embodiments or circumstances, the electronic circuit is open when in electrical contact with opposing terminals of the battery 120. In the depicted embodiment, the at least one electronic circuit includes a negative battery contact 132, which is configured to contact and electrically connect with an anode of the battery 120, and a positive battery contact 134, which is configured to contact and electrically connect to a cathode of the battery 120.

The battery 120 may be held in place by any suitable means. For example, a battery holder 115 (see FIG. 1B) may be disposed within the housing 110 and be shaped and sized to hold the battery 120 adjacent to the battery contacts 132, 134, even while an adjacent component, such as a pull tab, is displaced. In some embodiments, the battery holder 115 is formed from transparent material.

The electronic circuit and the battery 120 may be configured to perform or facilitate one or more operations. For example, the electronic circuit and battery 120 may be used to perform a computation, turn on a light, power a sensor, power a transmitter and/or accomplish any other electrically powered task.

Figure 2A:
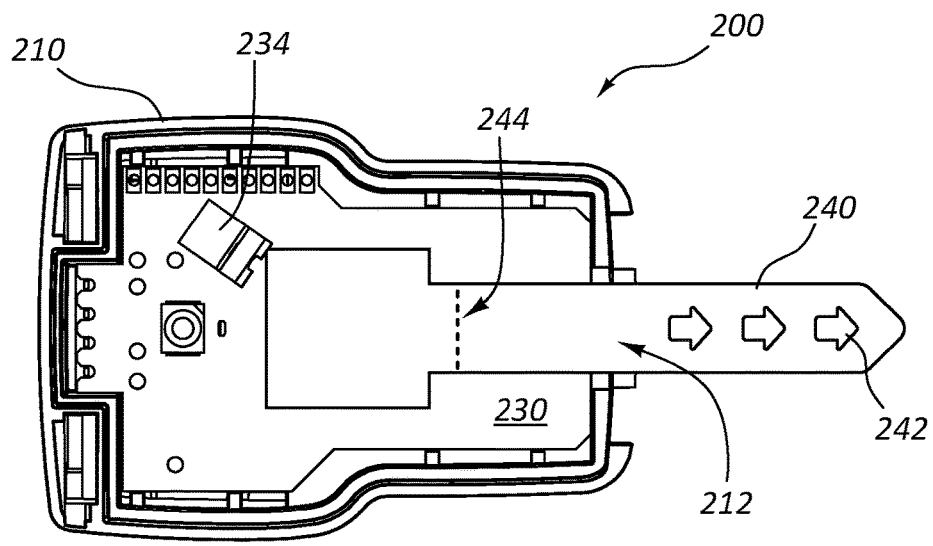
FIG. 2A is a top view of a portion of a pull tab assembly in an inoperable state, according to another embodiment.
Figure 2B:
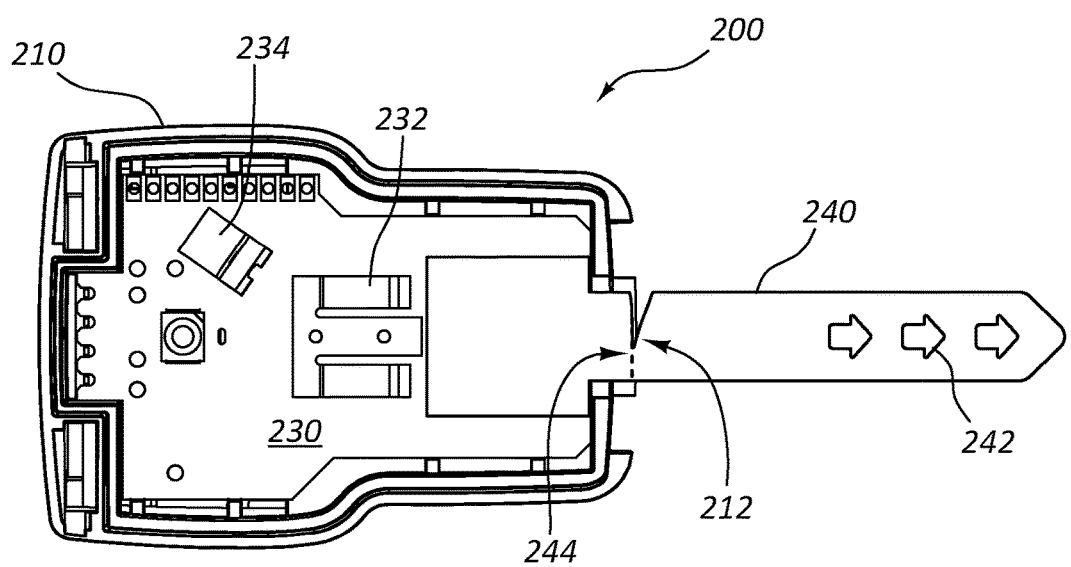
FIG. 2B is a top view of a portion of the pull tab assembly of FIG. 2A in an operable state.

FIGS. 2A and 2B depict a pull tab assembly 200 that resembles the assembly 100 described above in certain respects. Accordingly, like features are designated with like reference numerals, with the leading digits incremented to "2." For example, the embodiment depicted in FIGS. 2A-2B includes a housing 210 that may, in some respects, resemble the housing 110 of FIGS. 1A-1D. Relevant disclosure set forth above regarding similarly identified features thus may not be repeated hereafter. Moreover, specific features of assemblies and related components shown in FIGS. 1A-1D may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the pull tab assembly 200 and related components depicted in FIGS. 2A-2B. Any suitable combination of the features, and variations of the same, described with respect to the assembly 100 and related components illustrated in FIGS. 1A-1D can be employed with the pull tab assembly 200 and related components of FIG. 2A-2B, and vice versa. This pattern of disclosure applies equally to further embodiments depicted in subsequent figures and described hereafter, wherein the leading digits may be further incremented.

FIGS. 2A and 2B provide top views of a portion of the pull tab assembly 200 in different states. More particularly, FIG. 2A provides a top view a portion of the pull tab assembly 200 in an inoperable state, while FIG. 2B provides a top view of a portion of the pull tab assembly 200 in an operable state. The views provided in these figures are analogous to the view depicted in FIG. 1D, in which a cover of the housing 110, the battery holder 115, and a battery 120 are omitted to improve clarity. In other words, the battery of the pull tab assembly 200, if shown, would rest upon the distal portion of the pull tab 240 in FIG. 2A and would contact the negative battery contact 232 in FIG. 2B.

With reference to FIGS. 2A and 2B, the pull tab assembly 200 includes a housing 210, a battery (not shown), a circuit board 230, and a pull tab 240. The housing 210 is configured to substantially enclose the battery and the circuit board 230, thereby protecting the battery and circuit board 230 from the external environment. The housing 210 includes a slot 212 that extends through the housing 210, thereby providing a passageway between the interior of the housing 210 and the external environment.

The circuit board 230 includes at least one electronic circuit that is configured to electrically connect to opposite terminals of a battery. For example, in the depicted embodiment, a negative battery contact 232 of the electronic circuit is configured to contact and electrically connect to an anode of the battery, and a positive battery contact 234 is configured to contact and electrically connect to a cathode of the battery.

As depicted in FIG. 2A, the pull tab 240 is partially disposed within the housing 210. The pull tab 240 includes a distal portion that is sized and shaped to be disposed between the battery (not shown) and an underlying battery contact 232. The pull tab 240 may include or consist essentially of non-conductive material. For example, when the pull tab 240 is disposed as shown in FIG. 2A, a non-conductive distal portion of the pull tab 240 interrupts an electrical connection between the battery and the battery contact 232. Stated differently, the pull tab 240 may be used to selectively interrupt an electrical connection between the battery and other components, such as a battery contact 232 of the circuit board 230. Thus, FIG. 2A depicts a pull tab assembly 200 in which the battery (not shown) is electrically disconnected from a battery contact 232 due to the position of the pull tab 240. By leaving the pull tab assembly 200 in an inoperable state, such as that depicted in FIG. 2A, battery depletion may be minimized.

The pull tab 240 is configured to be at least partially withdrawn from the housing 210. For example, in the depicted embodiment, a proximal portion of the pull tab 240 is sized and shaped to pass through the slot 212 of the housing 210 as the pull tab 240 is retracted from the housing 210. Stated differently, the slot 212 of the housing 210 may have a width that is greater than the width of a proximal portion of the pull tab 240.

The pull tab 240 may include one or more indicia 242 that indicate the pull direction for at least partially withdrawing the pull tab 240 from the housing 210. For example, in the depicted embodiment, a proximal portion of the pull tab 240 includes a plurality of arrow-shaped cut-outs, with the tips of the arrows pointed in the pull direction. The one or more indicia 242 may be configured to provide improved grip to the pull tab 240. In some embodiments, such as that depicted in FIGS. 2A and 2B, such improved grip may arise as a result of indicia 242 that are cut out of the pull tab 240. In other or further embodiments, improved grip may result from one or more indicia that are raised from the surface of the pull tab. In still other embodiments, the one or more indicia are level with a flat surface of the pull tab and do not provide improved grip.

By partially withdrawing the pull tab 240 from the housing 210, the pull tab assembly 200 may transition from an inoperable state (FIG. 2A) to an operable state (FIG. 2B). In other words, the pull tab assembly 200 may transition to a state in which the battery forms an electrical connection with both a negative battery contact 232 and a positive battery contact 234 (FIG. 2B). For example, a practitioner may grasp a proximal portion of the pull tab 240 and pull on the pull tab 240 to partially withdraw the pull tab 240 from the housing 210. Withdrawal of the pull tab 240 displaces the pull tab 240 such that a distal portion of pull tab 240 is no longer disposed between the battery (not shown) and the battery contact 232. In other words, as the pull tab 240 is withdrawn, the position of the battery may remain largely unchanged (e.g., due to a battery holder analogous to that depicted in FIG. 1B) so that the battery contacts the negative battery contact 232. In other words, proximal displacement of the pull tab 240 may establish an electrical connection between the battery and the negative battery contact 232.

In the depicted embodiment, a distal portion of the pull tab 240 includes a width that is greater than the width of the slot 212 of the housing 210. Stated conversely, the housing 210 may include a slot 212 of a width that is less than the width of a distal portion of the pull tab 240. Thus, as the pull tab 240 is retracted in a proximal direction, the distal portion of the pull tab 240 may, due to the width of the distal portion, abut against housing 210, thereby preventing full withdrawal of the pull tab 240. Stated differently, the slot 212 may permit partial, but not full, withdrawal of the pull tab 240 from the housing 210.

The pull tab 240 may also include perforations 244 that facilitate tearing of the pull tab 240 into a plurality of segments. For example, once the pull tab 240 is withdrawn such that the distal portion of the pull tab 240 abuts against the walls of housing 210 that define the slot 212, the practitioner may tear the pull tab 240 along the perforations 244, thereby dividing the pull tab 240 into a plurality of segments. In this manner, the portion of the pull tab 240 that is disposed outside of the housing 210 when the pull tab 240 has been retracted (or a portion thereof) may be discarded, while a distal portion of the pull tab 240 remains inside of the housing 210. The portion of the pull tab 240 that remains associated with the pull tab assembly 200 may impede fluid entry into the housing 210. In other words, the passageway defined by the slot 212 may be obstructed by a portion of the pull tab 240 that remains in (or at least mostly within) the housing 210, thereby protecting the components disposed within the housing 210 from the external environment. Stated differently, at least a portion of the pull tab 240 may be configured to impede fluid entry through the slot 212 into the housing 210 after the pull tab 240 has been partially withdrawn such that the battery is in contact with both battery contacts 232, 234.

While, in the embodiment depicted in FIGS. 2A and 2B, the pull tab 240 is configured to selectively interrupt an electrical connection between a negative battery contact 232 and an anode of a battery, a similar mechanism may be employed to interrupt an electrical connection between a positive battery contact 234 and the cathode of a battery.

Figure 3A:
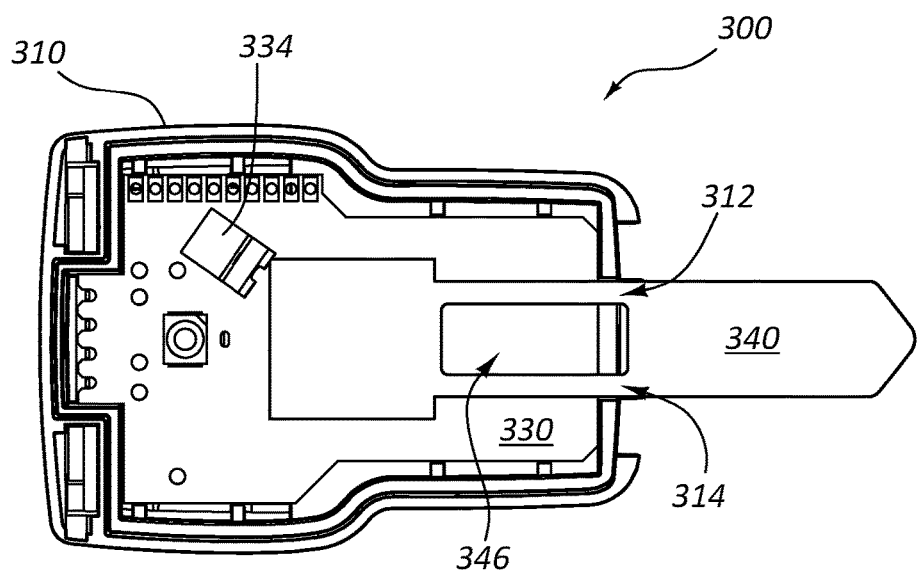
FIG. 3A is a top view of a portion of a pull tab assembly in an inoperable state, according to another embodiment.
Figure 3B:
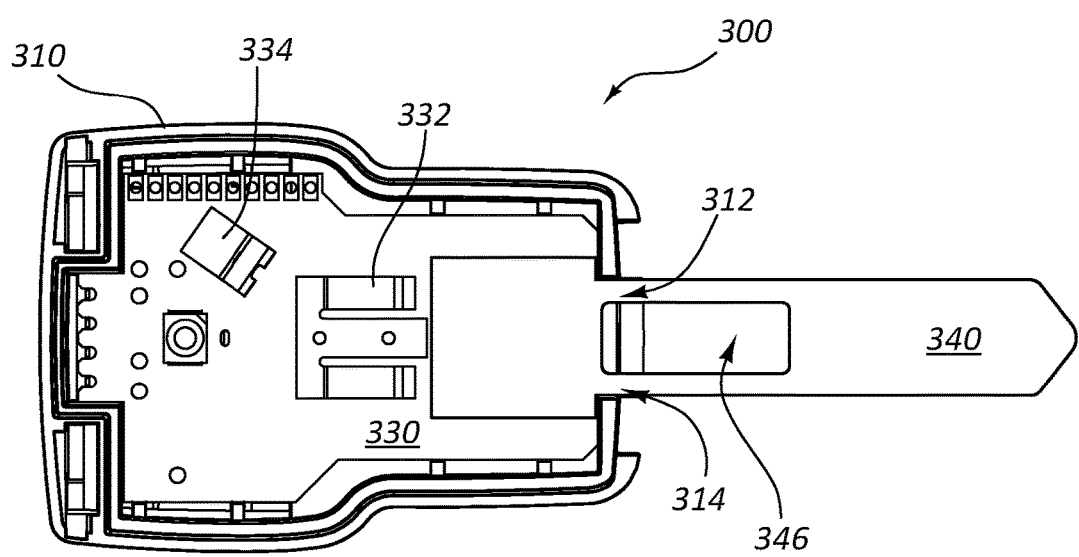
FIG. 3B is a top view of a portion of the pull tab assembly of FIG. 3A in an operable state.

FIGS. 3A and 3B provide top views of a portion of a pull tab assembly 300, according to another embodiment. More particularly, FIG. 3A illustrates the pull tab assembly 300 in an inoperable state, while FIG. 3B illustrates the pull tab assembly 300 in an operable state. These figures provide views that are analogous to the views provided in FIGS. 1D, 2A, and 2B, in which the features are omitted to improve clarity.

The pull tab assembly 300 includes a housing 310, a battery (not shown), a circuit board 330, and a pull tab 340. The housing 310 is configured to substantially enclose the battery, the circuit board 330, and other related components (such as one or more circuits of the circuit board 330). In the depicted embodiment, the housing 310 also includes a first slot 312 and a second slot 314. The slots 312, 314 are configured to facilitate at least partial withdrawal of the pull tab 340 from the housing 310.

The circuit board 330 includes at least one electronic circuit that is configured to electrically connect to opposite electrodes of a battery. For example, a negative battery contact 332 of the electronic circuit is configured to contact and electrically connect with an anode of the battery, and a positive battery contact 334 is configured to contact and electrically connect to a cathode of the battery.

The pull tab 340 may be configured to selectively interrupt an electrical connection between the battery and a battery contact 332. For example, the pull tab 340 may be configured to be partially withdrawn from the housing, thereby permitting contact between a battery and a battery contact 332 that was previously covered by the pull tab 340. Partial withdrawal of the pull tab 340 in this manner may transition the device from an inoperable state (FIG. 3A) to an operable state (FIG. 3B).

For example, a practitioner may grasp the pull tab 340 and draw the pull tab 340 in a proximal direction. By drawing the pull tab 340 in a proximal direction, a distal portion of the pull tab 340 that was disposed between the battery and the battery contact 332 is displaced, allowing the battery to contact the negative battery contact 332. In this manner, the pull tab 340 may transition from a state in which the battery is not in contact with the negative battery contact 332 to a state in which the battery is in contact with both the negative battery contact 332 and the positive battery contact 334.

The pull tab 340 may include an aperture 346 and elongate regions or portions disposed lateral of the aperture 346. Stated differently, the pull tab 340 may include a first portion that is disposed on a first side of the aperture 346, and a second portion that is disposed on a second side of the aperture 346 that is opposite of the first side. The portions of the pull tab 340 that are disposed on opposite sides of the aperture 346 may each be configured to pass through separate housing slots 312, 314 as the pull tab 340 is withdrawn. For example, the first portion of pull tab 340 that is disposed on a first side of the aperture 346 may be configured to pass through a first slot 312, while a second portion of the pull tab 340 that is disposed on the opposite side of the aperture 346 may be configured to pass through a second slot 314. In this manner, slots 312, 314 of relatively short width may be used, while still enabling partial withdrawal of the pull tab 340 from the housing 310. Slots of relatively short width, such as slots 312, 314, may minimize or otherwise reduce entry of contaminating fluid into the interior of the housing 310.

Figure 4A:
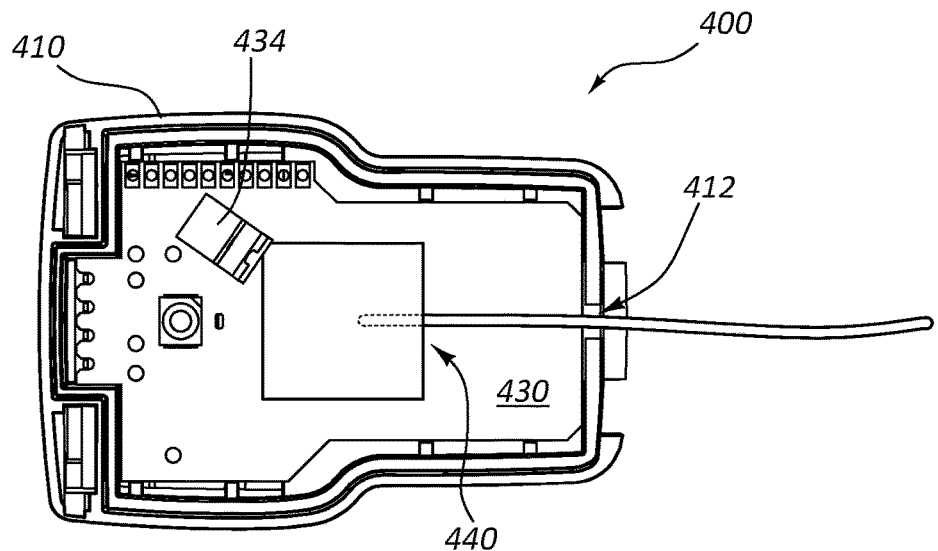
FIG. 4A is a top view of a portion of a pull tab assembly in an inoperable state, according to another embodiment.
Figure 4B:
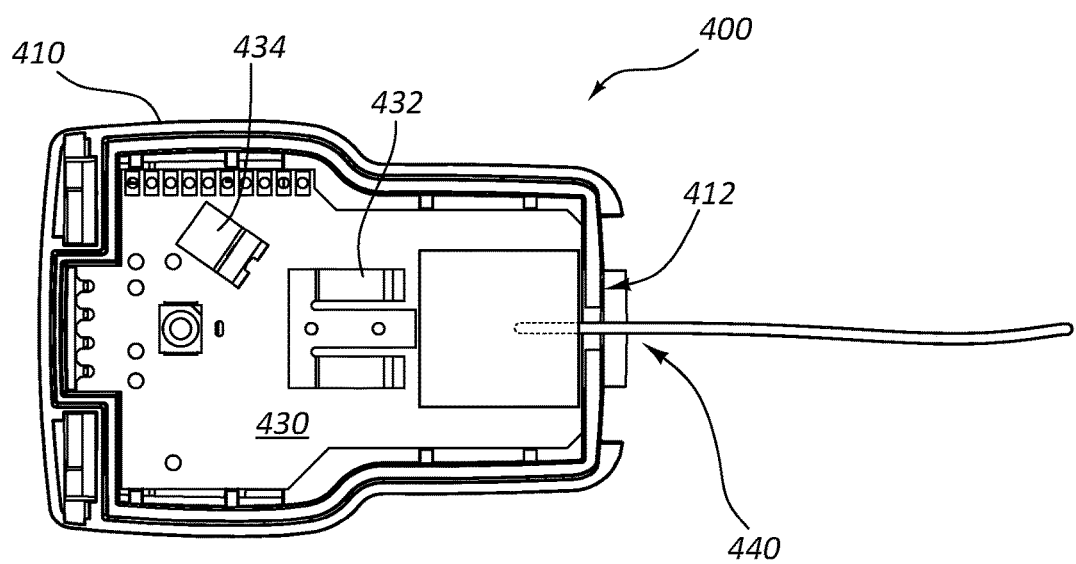
FIG. 4B is a top view of a portion of the pull tab assembly of FIG. 4A in an operable state.

FIGS. 4A and 4B provide top views of a portion of a pull tab assembly 400, according to another embodiment. More particularly, FIG. 4A illustrates the pull tab assembly 400 in an inoperable state, while FIG. 4B illustrates the pull tab assembly 400 in an operable state. These figures provide views that are analogous to other views in which the battery is omitted to provide improved clarity.

The pull tab assembly 400 includes a housing 410, a battery (not shown), a circuit board 430, and a pull tab 440. The housing 410 is configured to substantially enclose the battery, the circuit board 430, and other related components (such as the one or more circuits of the circuit board 430). In the depicted embodiment, the housing 410 also includes a slot 412 that is configured to facilitate at least partial withdrawal of the pull tab 440 from the housing 410.

The circuit board 430 includes at least one electronic circuit that is configured to electrically connect to opposite electrodes of a battery. For example, a negative battery contact 432 of the electronic circuit is configured to contact and electrically connect with an anode of the battery, and a positive battery contact 434 is configured to contact and electrically connect to a cathode of the battery.

The pull tab 440 includes a distal portion that is configured to selectively interrupt an electrical connection between the battery and a battery contact, such as the negative battery contact 432. The pull tab 440 also includes a proximal portion that is attached to the distal portion. The proximal portion of the pull tab 440 is configured to facilitate displacement of the distal portion of the pull tab 440 within the housing 410. For example, in the depicted embodiment, the proximal portion of the pull tab 440 includes or consists of a string or wire. The string or wire may be attached to the distal portion of the pull tab 440 in any suitable manner. As a practitioner grasps the string or wire and draws the string or wire in a proximal direction, the distal portion of the pull tab 440 may be displaced, thereby allowing the battery to form an electrical connection with the underlying battery contact 432.

The slot 412 is sized and shaped to permit passage of the string or wire through the slot, but is sufficiently narrow to prevent complete withdrawal of the pull tab 440 from the housing 410. Because wires and strings are generally of narrow width, pull tabs that include such wires or strings may allow for the use of relatively narrow slots, which in turn reduces the likelihood of contaminant entry through the slot 412.

Figure 5A:
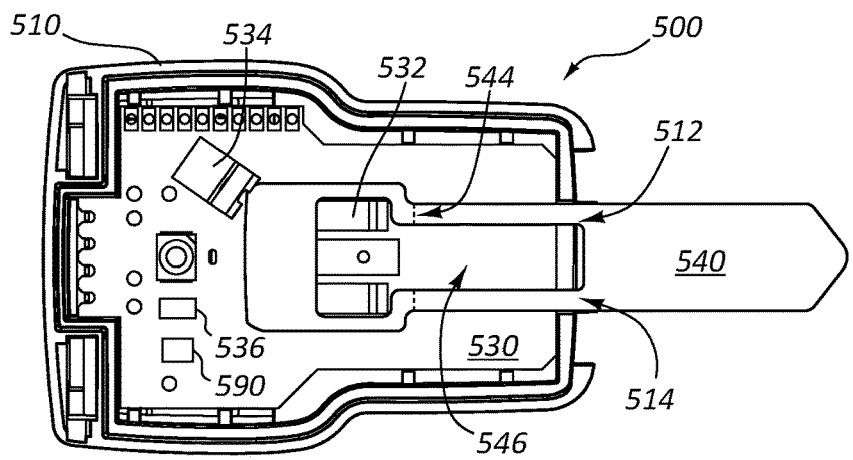
FIG. 5A is a top view of a portion of a pull tab assembly in an operable state, according to another embodiment.
Figure 5B:
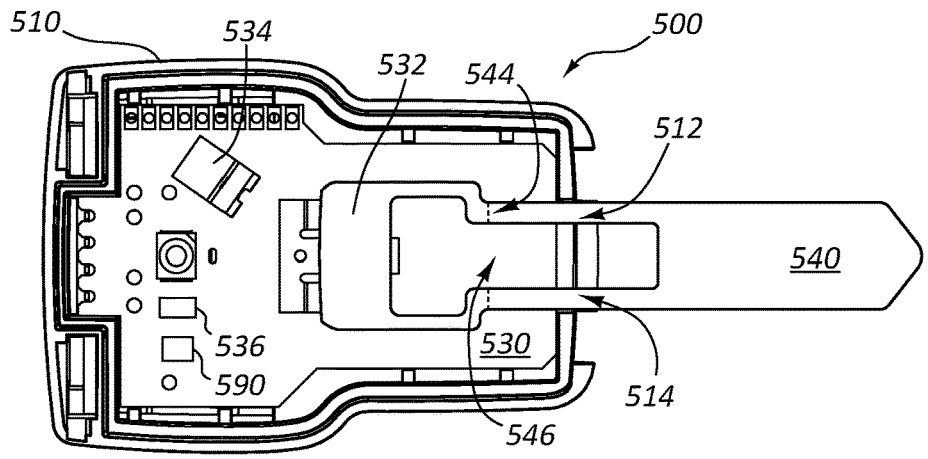
FIG. 5B is a top view of a portion of the pull tab assembly of FIG. 5A in an inoperable state.
Figure 5C:
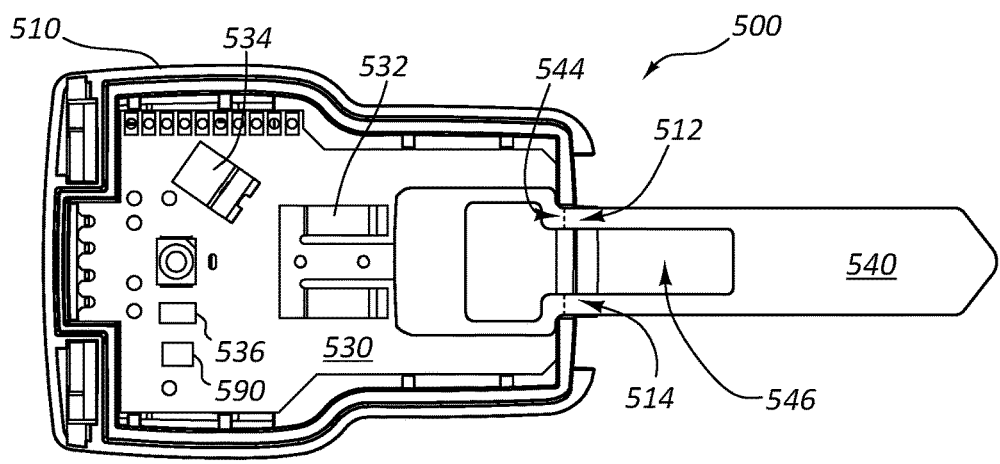
FIG. 5C is a top view of a portion of the pull tab assembly of FIG. 5A in another operable state.

FIGS. 5A-5C provide top views of a portion of a pull tab assembly 500, according to another embodiment. More particularly, FIG. 5A illustrates the pull tab assembly 500 in an operable state, FIG. 5B illustrates the pull tab assembly 500 in an inoperable state, and FIG. 5C illustrates the pull tab assembly 500 in another operable state. These figures provide views that are analogous to other views in which elements (e.g., a battery, battery holder, a housing cover) are omitted to provide improved clarity.

The pull tab assembly 500 includes a housing 510, a battery (not shown), a circuit board 530, a rewritable memory 536, a transmitter 590, and a pull tab 540. The housing 510 is configured to substantially enclose the battery, the circuit board 530, the rewritable memory 536, the transmitter 590, and one or more circuits of the circuit board 530. In the depicted embodiment, the housing also includes a first slot 512 and a second slot 514. The slots 512, 514 are configured to facilitate at least partial withdrawal of the pull tab 540 from the housing 510.

The circuit board 530 includes at least one electronic circuit that is configured to electrically connect to opposite electrodes of a battery. For example, a negative battery contact 532 of the electronic circuit is configured to contact and electrically connect with an anode of the battery, and a positive battery contact 534 is configured to contact and electrically connect to a cathode of the battery.

The pull tab 540 includes a distal portion that is configured to selectively interrupt an electrical connection between a battery and a battery contact 532. The pull tab 540 also includes an aperture 546 that extends through both a first (e.g., upper) surface of the pull tab and a second (e.g., lower) surface of the pull tab 540. The aperture 546 is shaped such that a proximal portion of the aperture 546 is narrower than a distal portion of the aperture 546. Elongate portions of the pull tab 540 that are disposed lateral of the proximal portion of the aperture 546 are configured to pass through separate housing slots 512, 514 as the pull tab 540 is partially withdrawn from the housing. A distal portion of the aperture 546 may be sized and shaped such that a battery may contact the battery contact 532 through the aperture 546 when the assembly 500 is in an operable state (see FIG. 5A).

The pull tab assembly 500 is configured to transition from a first (operable) state (see FIG. 5A) to a second (inoperable) state (see FIG. 5B) and subsequently transition from the second (inoperable) state (see FIG. 5B) to the first (operable) state (see FIG. 5C) as the pull tab 540 is displaced relative to the battery and the battery contact 532. Stated differently, as the pull tab 540 is at least partially withdrawn from the housing 510, the pull tab assembly 500 first transitions from a state in which the battery is in electrical contact with the negative battery contact 532 (see FIG. 5A) to a state in which the battery is not in electrical contact with the negative battery contact 532 (see FIG. 5B) and then transitions back to a state in which the battery is in electrical contact with the negative battery contact 532 (see FIG. 5C). In the depicted embodiment, this transition process can be accomplished as the pull tab 540 is withdrawn in a single direction.

Stated differently, the pull tab 540 includes an aperture 546 that extends from a first (e.g., upper) side of the pull tab 540 to a second (e.g., lower) side of the pull tab 540. The aperture is configured to permit electrical contact between the battery and a battery contact 532 through the aperture 546 (see FIG. 5A). The pull tab 540 also includes a non-conductive solid portion that is disposed distal of the aperture 546. This solid portion of the pull tab is configured to disrupt electrical contact between the battery and the battery contact (see FIG. 5B).

The rewritable memory 536 of the pull tab assembly 500 may be configured to be programmed while the rewritable memory 536 is substantially enclosed within the housing 510. For example, the transmitter 590 (which may also be substantially enclosed within the housing 510) may receive a wireless signal sent from a source disposed outside of the pull tab assembly 500. The transmitter 590 may, in turn, send or relay a signal (e.g., through the circuit board 530) to the rewritable memory 536, thereby altering instructions stored on the rewritable memory 536. Stated differently, the rewritable memory 536 may be wirelessly programmed while the rewritable memory 536 is enclosed within the housing 510. One of ordinary skill in the art, with the benefit of this disclosure, will recognize that other suitable methods for wirelessly programming a memory within the housing are within the scope of this disclosure.

Figure 6:
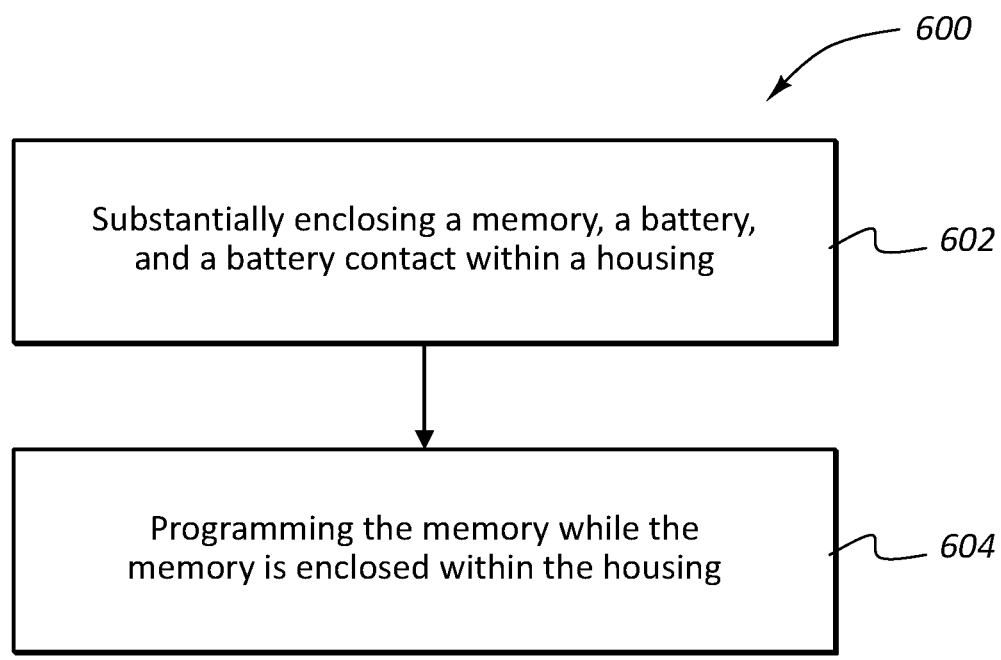
FIG. 6 is a block diagram of a method of assembling a pull tab assembly or device.

The embodiment depicted in FIGS. 5A-5C may be used to carry out one or more methods, such as the method 600 depicted in FIG. 6. The method 600 is a method of assembling a pull tab assembly or device for interrupting an electrical connection with a battery. In the illustrated embodiment, the method 600 includes a step 602 of substantially enclosing a memory, a battery, a pull tab, and an electrical circuit within a housing. The method 600 also includes another step 604 of programming the memory while the memory is enclosed within the housing.

A device or assembly, such as pull tab assembly 500, that has been assembled by the above-described method may then be manipulated by at least partially withdrawing the pull tab from the housing. Such partial withdrawal of the pull tab from the housing may cause the device or assembly to transition from a state in which the battery is not in contact with both a first battery contact and a second battery contact (such as that depicted in FIG. 5B) to a state in which the battery is in contact with both the first battery contact and the second battery contact (such as that depicted in FIG. 5C). Withdrawal of the pull tab may also cause the device or assembly to transition from a state in which the battery is in contact with both a first battery contact and a second battery contact (such as that depicted in FIG. 5A) to a state in which the battery is not in contact with both the first battery contact and the second battery contact (such as that depicted in FIG. 5B).

The pull tab 540 may also include perforations 544 that facilitate tearing of the pull tab 540 into a plurality of segments. For example, once the pull tab 540 is withdrawn such that the distal portion of the pull tab 540 abuts against the walls of housing 510 that define the slot 512, the practitioner may tear the pull tab 540 along the perforations 544, thereby dividing the pull tab 540 into a plurality of segments. In this manner, the portion of the pull tab 540 that is disposed outside of the housing 510 when the pull tab 540 has been retracted (or a portion thereof) may be discarded, while a distal portion of the pull tab 540 remains inside of the housing 510. The portion of the pull tab 540 that remains associated with the pull tab assembly 500 may impede fluid entry into the housing 510. In other words, the passageway defined by the slot 512 may be obstructed by a portion of the pull tab 540 that remains in (or at least mostly within) the housing 510, thereby protecting the components disposed within the housing 510 from the external environment. Stated differently, at least a portion of the pull tab 540 may be configured to impede fluid entry through the slot 512 into the housing 510 after the pull tab 540 has been partially withdrawn such that the battery is in contact with both battery contacts 532, 534.

Figure 7A:
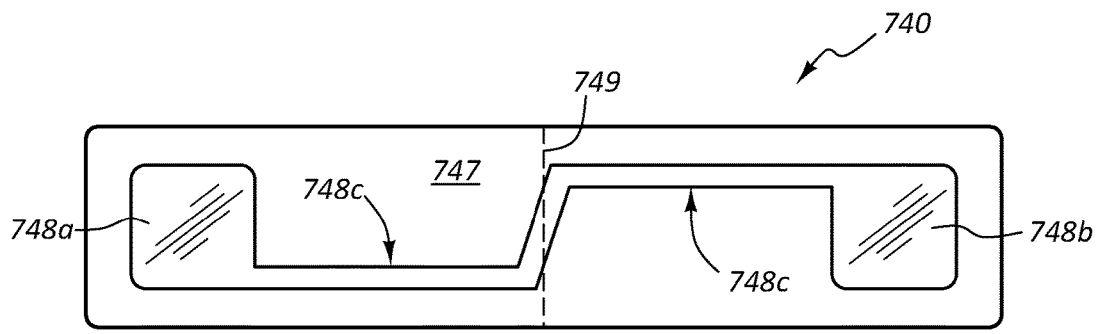
FIG. 7A is a top view of a pull tab.
Figure 7B:
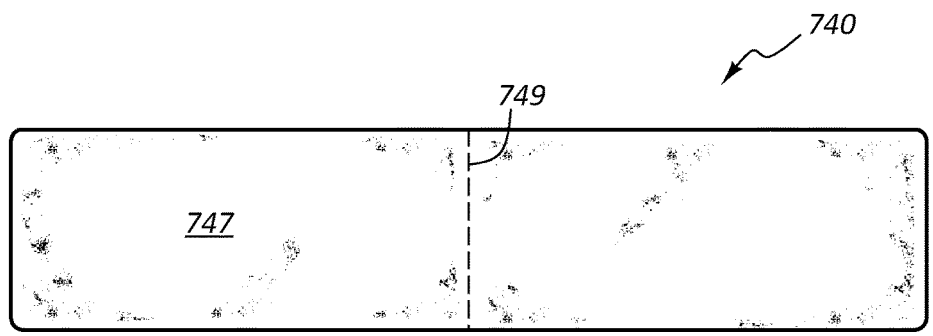
FIG. 7B is a bottom view of the pull tab of FIG. 7A.
Figure 7C:
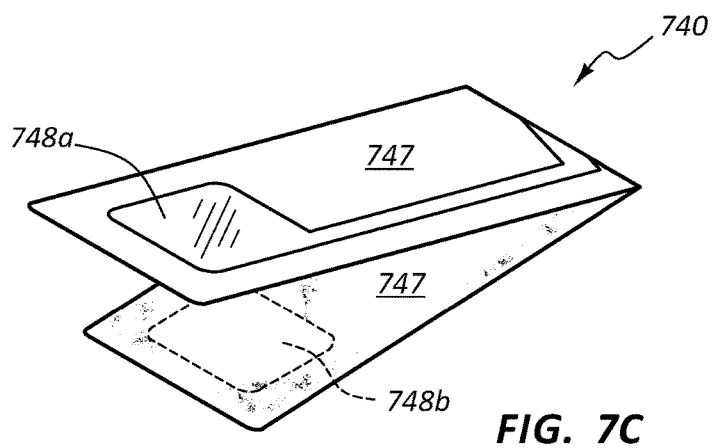
FIG. 7C is a perspective view of the pull tab of FIG. 7A in a folded state.

FIGS. 7A-7C depict alternative views of a pull tab 740. More particularly, FIG. 7A provides a top view of a pull tab 740. FIG. 7B provides a bottom view of the pull tab 740. And FIG. 7C provides a perspective view of the pull tab 740 in a partially folded state.

As depicted in FIG. 7A, the pull tab 740 may include a non-conductive surface 747 and a conductive surface 748. For example, the pull tab 740 may include a non-conductive surface 747 upon which conductive material (e.g., conductive ink) may be deposited or arranged to form a conductive surface 748. The conductive surface 748 may be arranged in any suitable fashion on the non-conductive surface 747. For example, in the depicted embodiment, a first contact region 748a of conductive material is disposed adjacent a first end of the surface 747 while a second contact region 748b of conductive material is disposed adjacent an opposite end of the non-conductive surface 747. The two regions are connected by a path 748c of conductive material. Stated differently, the first contact region 748a and the second contact region 748b are electrically connected via the path 748c. In the depicted embodiment, the path 748c includes two portions that are (1) parallel to one another and (2) offset from one another. These portions of the path 748c are connected by a middle portion that connects the parallel portions. In other embodiments, analogous portions of the path are not offset from one another (e.g., the path is a single straight line). In still other embodiments, the entire top surface of the pull tab is a conductive surface.

As depicted in FIG. 7B, the opposite (e.g., bottom) side of the pull tab 740 presents a non-conductive surface 747. Stated differently, the non-conductive surface 747 may be disposed opposite of the conductive surface 748.

As depicted in FIG. 7C, opposite sides of the non-conductive back surface 747 of the pull tab 740 may be bent or folded toward one another, with the conductive surfaces 748 displayed on the outside of the pull tab 740. For example, the pull tab 740 may be folded along line 749 as the non-conductive surfaces 747 are displaced toward one another. In some embodiments, the non-conductive surfaces 747 on the bottom of the pull tab 740 adhere to one another.

Figure 8A:
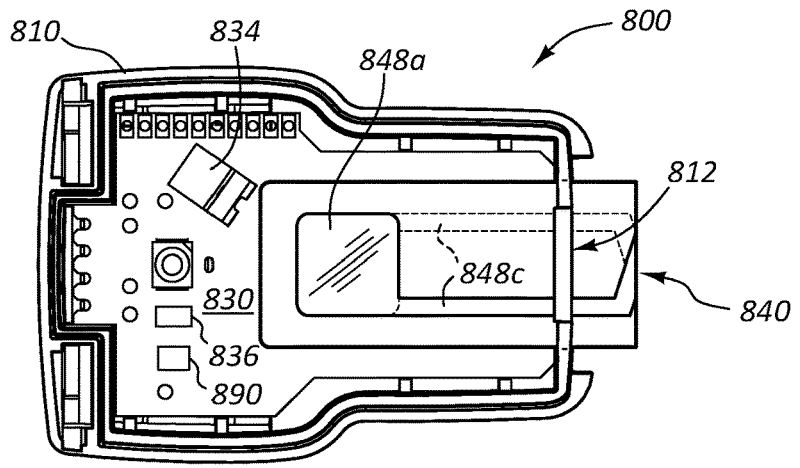
FIG. 8A is a top view of a portion of a pull tab assembly, according to another embodiment.
Figure 8B:
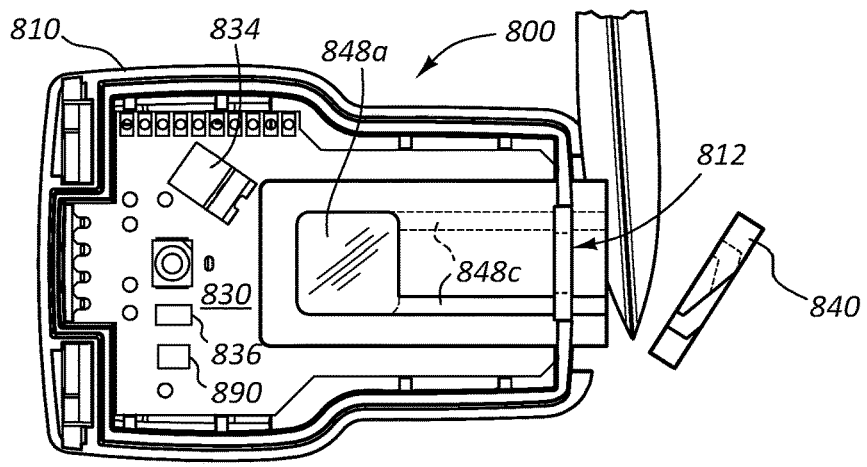
FIG. 8B is a top view of a portion of the pull tab assembly of FIG. 8A, depicting removal of a proximal region of the pull tab.
Figure 8C:
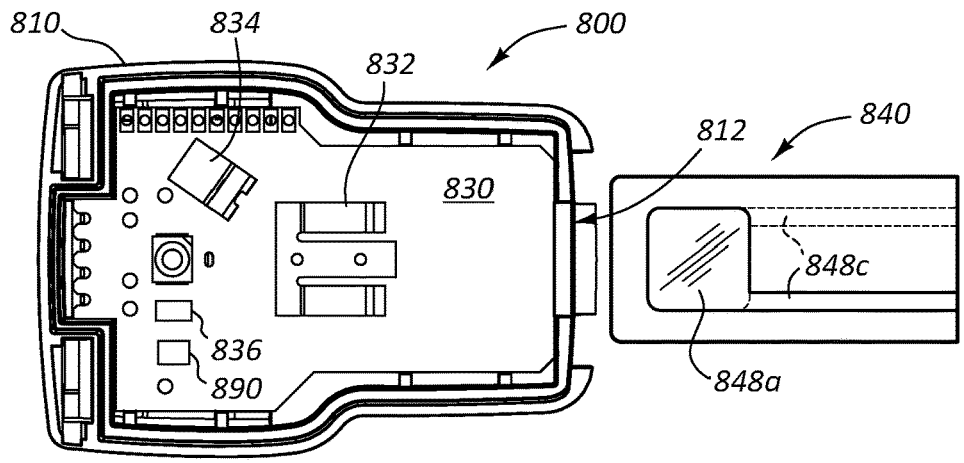
FIG. 8C is a top view of a portion of the pull tab assembly of FIG. 8A subsequent to withdrawal of the pull tab.

FIGS. 8A-8C provide top views of a portion of a pull tab assembly 800, according to another embodiment. More particularly, FIG. 8A illustrates the pull tab assembly 800 in an operable state. FIG. 8B illustrates the pull tab assembly 800 in an inoperable state, and FIG. 8C illustrates the pull tab assembly 800 in another operable state. These figures provide views that are analogous to other views in which elements, such as a battery, battery holder, and/or a housing cover, are omitted to provide improved clarity.

With reference to FIGS. 8A-8C, the pull tab assembly 800 includes a housing 810, a battery (not shown), a circuit board 830, a rewritable memory 836, a transmitter 890, and a pull tab 840. The housing 810 is configured to substantially enclose the battery, the rewritable memory 836, the transmitter 890, and the circuit board 830. In the depicted embodiment, the housing 810 also includes slot 812 that is configured to facilitate withdrawal of the entirety of the pull tab 840 from the housing 810.

The circuit board 830 includes at least one electronic circuit that is configured to electrically connect to opposite electrodes of a battery. For example, a negative battery contact 832 of the electronic circuit is configured to contact and electrically connect with an anode of the battery, and a positive battery contact 834 is configured to contact and electrically connect to a cathode of the battery.

The rewritable memory 836 may be programmed while enclosed within the housing 810. For example, a wireless signal may be sent to a transmitter 890, which in turn sends or relays a signal to the rewritable memory 836, thereby altering the instructions stored thereon.

The pull tab 840 is analogous to the pull tab 740 disclosed in FIGS. 7A-7C. For example, in FIGS. 8A-8C, the pull tab 840 is folded on itself and includes a first contact region 848a and a second contact region (not shown) that are connected by a path 848c.

When in the configuration depicted in FIG. 8A, the battery of the pull tab assembly 800 is electrically connected to the negative battery contact 832, as the pull tab 840 provides a conductive surface 848 that extends from the anode of the battery to the negative battery contact 832. Stated differently, the conductive surface 848 of the pull tab 840 causes the battery to be in electrical communication with the negative battery contact 832.

The electrical connection between the battery and the negative battery contact 832 may be interrupted by cutting or removing a proximal portion of the pull tab 840 (e.g., the portion of the pull tab 840 that includes the fold). For example, as depicted in FIG. 8B, the proximal end of the pull tab 840 may be cut, thereby disrupting the electrical connection between the battery and battery contact 832. In the depicted embodiment, once the proximal portion of the pull tab 840 is removed, the portions of the path 848c on each side of the pull tab 840 are not aligned with one another, thereby minimizing the likelihood of inadvertent contact between the now-separated portions of the conductive path 848c. In this manner, cutting or removal of a proximal portion of the pull tab 840 may transition the pull tab assembly 800 from a first state in which the battery is in contact and electrical communication with the negative battery contact 832 to a second state in which the battery is not in contact and electrical communication with the negative battery contact 832.

Once the proximal portion of the pull tab 840 has been cut or removed such that the assembly 800 is in a second state in which the battery is not electrically connected to the negative battery contact 832, the remaining portion(s) of the pull tab 840 may be withdrawn from the housing 810 (see FIG. 8C), thereby allowing the battery to contact and electrically connect to the negative battery contact 832.

Stated differently, the pull tab assembly 800 may transition from an operable state to an inoperable state as a result of cutting or removal of a proximal portion of the pull tab 840. The pull tab assembly 800 may subsequently transition from an inoperable state to an operable state as a result of displacement of the pull tab 840.

Figure 9:
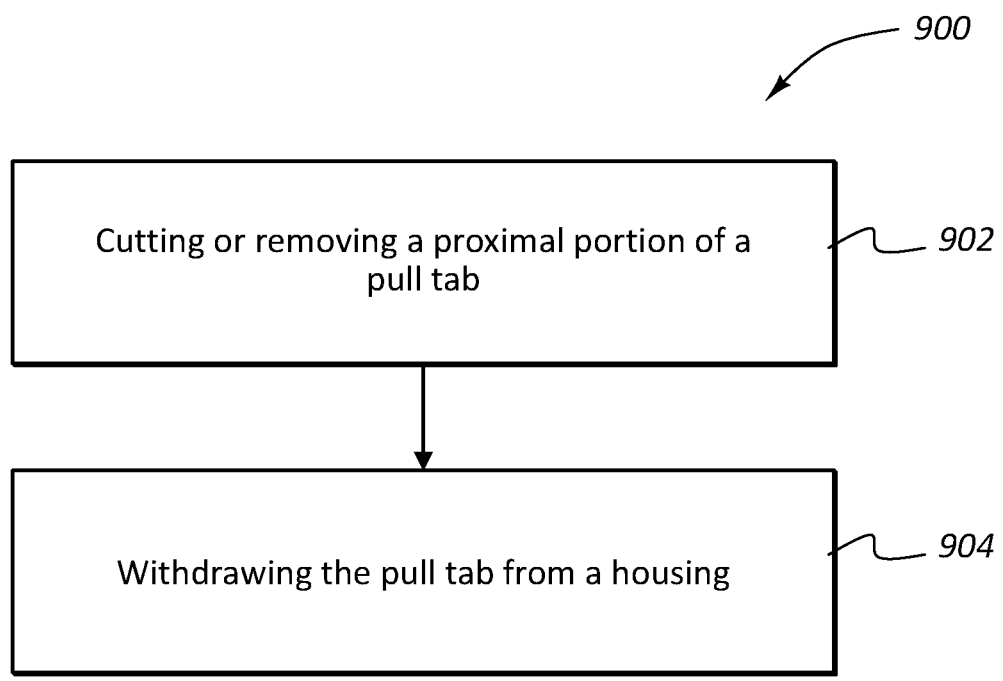
FIG. 9 is a block diagram of a method of interrupting and establishing an electrical connection between a battery and a battery contact.

In other words, a method of interrupting and reestablishing an electrical connection between a battery and a battery contact, such as the method 900 depicted in FIG. 9, may include the step 902 of cutting or removing a proximal portion of a pull tab, wherein cutting or removing of the proximal portion of the pull tab interrupts an electrical connection between the battery and the battery contact. The method 900 may further include the step 904 of displacing the pull tab after cutting or removing the proximal portion of the pull tab, thereby reestablishing an electrical connection between the battery and the battery contact.

Figure 10A:
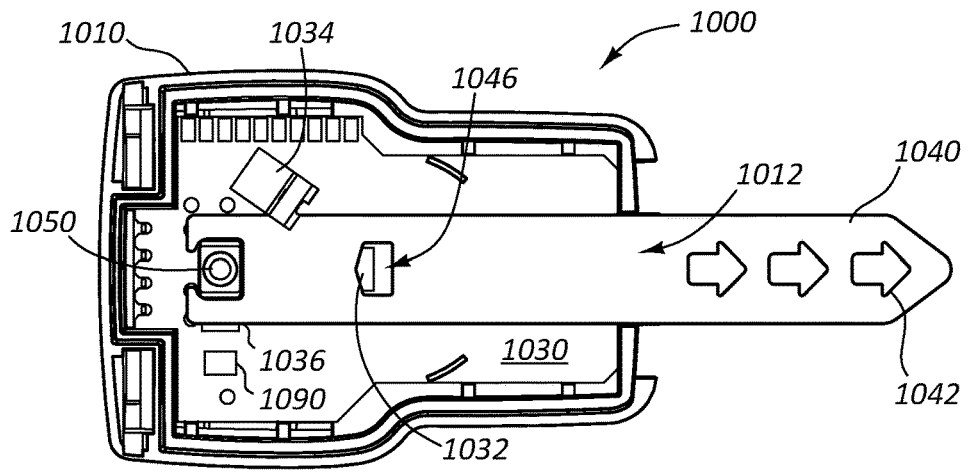
FIG. 10A is a top view of a portion of a pull tab assembly in an operable state, according to another embodiment.
Figure 10B:
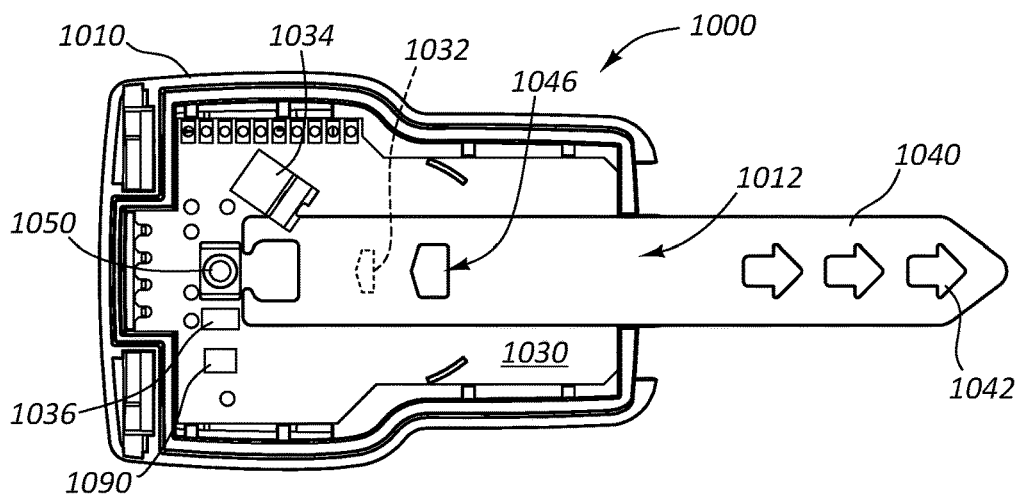
FIG. 10B is a top view of a portion of the pull tab assembly of FIG. 10A in an inoperable state.
Figure 10C:
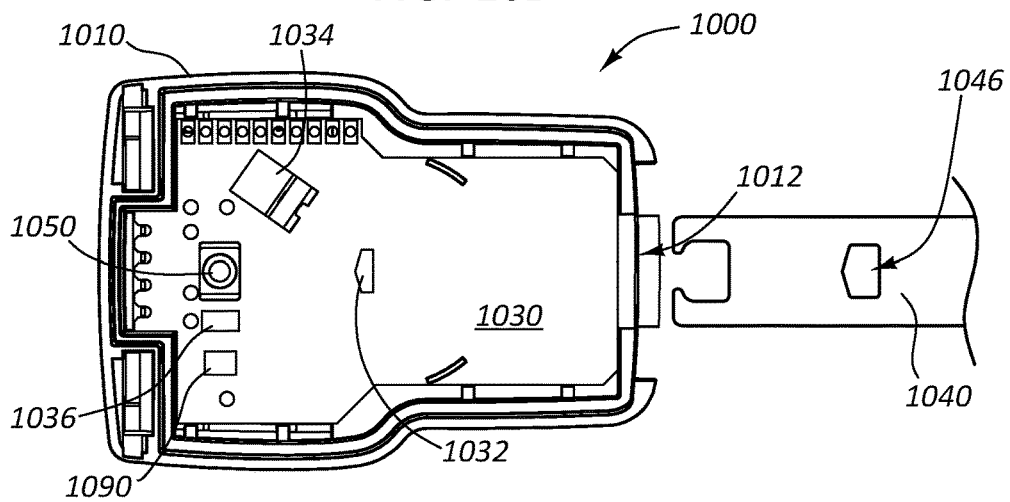
FIG. 10C is a top view of a portion of the pull tab assembly of FIG. 10A in another operable state.

FIGS. 10A-10C provide top views of a portion of a pull tab assembly 1000, according to another embodiment. More particularly, FIG. 10A illustrates the pull tab assembly 1000 in an operable state, FIG. 10B illustrates the pull tab assembly 1000 in an inoperable state, and FIG. 10C illustrates the pull tab assembly 1000 in another operable state. These figures provide views that are analogous to other views in which the elements, such as a battery, a battery holder, and/or a housing cover, are omitted to provide improved clarity.

The pull tab assembly 1000 includes a housing 1010, a battery (not shown), a circuit board 1030, a rewritable memory 1036, a transmitter 1090, and a pull tab 1040. The housing 1010 is configured to substantially enclose the battery, the circuit board 1030, the rewritable memory 1036, and the transmitter 1090. In the depicted embodiment, the housing also includes a slot 1012. The slot 1012 is configured to facilitate withdrawal of an entirety of the pull tab 1040 from the housing 1010.

The circuit board 1030 includes at least one electronic circuit that is configured to electrically connect to opposite electrodes of a battery. For example, a negative battery contact 1032 of the electronic circuit is configured to contact and electrically connect with an anode of the battery, and a positive battery contact 1034 is configured to contact and electrically connect to a cathode of the battery.

The rewritable memory 1036 may be programmed while the rewritable memory 1036 is enclosed within the housing 1010. For example, the transmitter 1090 may receive a wireless signal from a source disposed outside of the pull tab assembly 1000 and send or relay that signal (or generate and send some other signal) to the rewritable memory 1036, thereby altering the instructions stored thereon.

The pull tab 1040 includes a distal portion that is configured to extend around a majority of a structural support element, such as a status indicator 1050. Stated differently, the pull tab 1040 may include a distal portion that is configured to extend around a majority of a cross-sectional profile of the status indicator 1050. The distal portion of the pull tab 1040 may hold the pull tab 1040 in place until a proximal force of sufficient magnitude is applied to the pull tab 1040, thereby causing the distal portion of the pull tab 1040 to deflect laterally such that the pull tab 1040 can be displaced in a proximal direction. In other words, the pull tab 1040 (or a distal portion thereof) may be formed from material with sufficient flexibility such that the pull tab 1040 may deflect around the status indicator 1050 as the pull tab 1040 is withdrawn.

The pull tab 1040 may also include an aperture 1046 that extends through both a first (e.g., upper) surface of the pull tab and a second (e.g., lower) surface of the pull tab 1040. The aperture 1046 is sized and shaped such that a battery may contact the battery contact 1032 through the aperture 1046 when the pull tab assembly 1000 is in the operable state depicted in FIG. 10A.

As depicted in FIGS. 10A-10C, the pull tab 1040 may also include a non-conductive solid portion that is disposed distal of the aperture 1046. This solid portion of the pull tab 1040 is configured to disrupt electrical contact between the battery and the battery contact 1032 when the pull tab assembly 1000 is in the state depicted in FIG. 10B.

The pull tab 1040 may also include one or more indicia 1042 that indicate the pull direction for withdrawing the pull tab 1040 from the housing 1010. For example, in the depicted embodiment, a proximal portion of the pull tab 1040 includes a plurality of arrow-shaped cut-outs, with the tips of the arrows pointed in the pull direction. The one or more indicia 1042 may be configured to provide improved grip to the pull tab 1040. In some embodiments, such as that depicted in FIGS. 10A-10C, such improved grip may arise as a result of indicia 1042 that are cut out of the pull tab 1040.

The pull tab assembly 1000 is configured to transition from a first (operable) state (see FIG. 10A) to a second (inoperable) state (see FIG. 10B) and subsequently transition from the second (inoperable) state (see FIG. 10B) to the first (operable) state (see FIG. 10C) as the pull tab 1040 is displaced relative to the battery and the battery contact 1032. Stated differently, as the pull tab 1040 is withdrawn from the housing 1010, the pull tab assembly 1000 first transitions from a state in which the battery is in electrical contact with the negative battery contact 1032 (see FIG. 10A) to a state in which the battery is not in electrical contact with the negative battery contact 1032 (see FIG. 10B) and then transitions back to a state in which the battery is in electrical contact with the negative battery contact 1032 (see FIG. 10C). In the depicted embodiment, this transition process can be accomplished as the pull tab 1040 is withdrawn in a single direction.

Figure 10D:
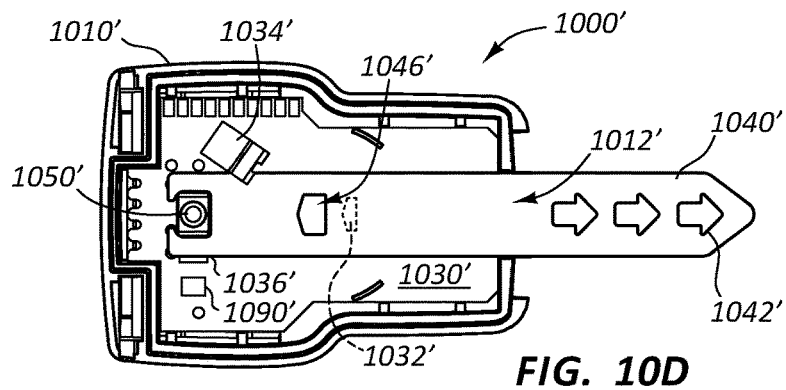
FIG. 10D is a top view of a portion a pull tab assembly in an inoperable state, according to another embodiment.
Figure 10E:
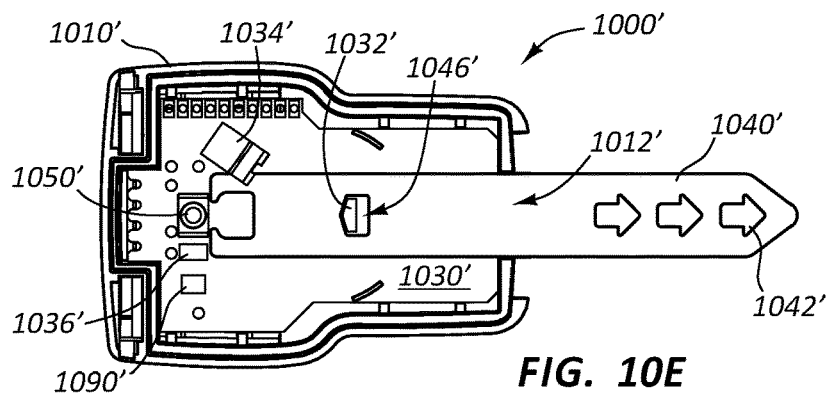
FIG. 10E is a top view of a portion of the pull tab assembly of FIG. 10D in an operable state.
Figure 10F:
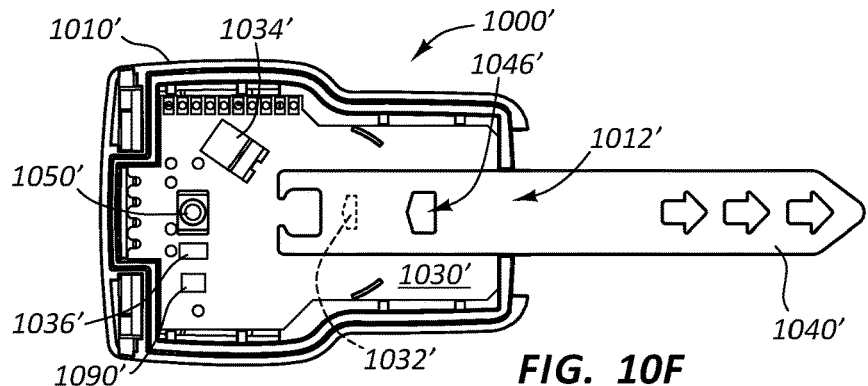
FIG. 10F is a top view of a portion of the pull tab assembly of FIG. 10D in another inoperable state.
Figure 10G:
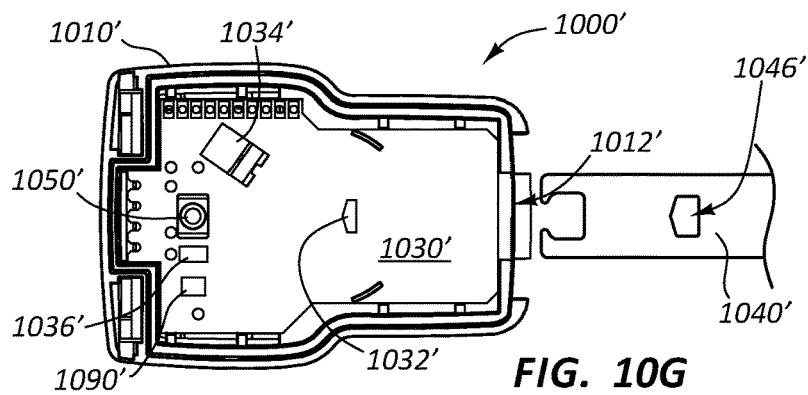
FIG. 10G is a top view of a portion of the pull tab assembly of FIG. 10D in another operable state.

FIGS. 10D-10E provide top views of a portion of a another pull tab assembly 1000', according to another embodiment. More particularly, FIG. 10D illustrates the pull tab assembly 1000' in an inoperable state, FIG. 10E illustrates the pull tab assembly 1000' in an operable state, FIG. 10F illustrates the pull tab assembly 1000' in another inoperable state, and FIG. 10G illustrates the pull tab assembly 1000' in another operable state. These figures provide views that are analogous to other views in which the elements, such as a battery, a battery holder, and/or a housing cover, are omitted to provide improved clarity. Further, the embodiment of FIGS. 10D-10E may be understood as analogous to the embodiments of FIGS. 10A-10C in many aspects. As compared to the embodiment of FIGS. 10A-10C, and as detailed below, the relative positions of the negative battery contact 1032' and aperture 1046' are configured such that the pull tab assembly 1000' transitions from an inoperable state, to an operable state, to another inoperable state, and to another operable state as the pull tab 1040' is withdrawn from the housing 1010'. As described above, the pull tab assembly 1000 of FIGS. 10A-10C transitions from an operable state, to an inoperable state, to another operable state as the pull tab 1040 is withdrawn from the housing 1010.

In the illustrated embodiment, the pull tab assembly 1000' includes a housing 1010', a battery (not shown), a circuit board 1030', a rewritable memory 1036', a transmitter 1090', and a pull tab 1040'. The housing 1010' is configured to substantially enclose the battery, the circuit board 1030', the rewritable memory 1036', and the transmitter 1090'. In the depicted embodiment, the housing also includes a slot 1012'. The slot 1012' is configured to facilitate withdrawal of an entirety of the pull tab 1040' from the housing 1010'.

The circuit board 1030' includes at least one electronic circuit that is configured to electrically connect to opposite electrodes of a battery. For example, a negative battery contact 1032' of the electronic circuit is configured to contact and electrically connect with an anode of the battery, and a positive battery contact 1034' is configured to contact and electrically connect to a cathode of the battery.

The rewritable memory 1036' may be programmed while the rewritable memory 1036' is enclosed within the housing 1010'. For example, the transmitter 1090' may receive a wireless signal from a source disposed outside of the pull tab assembly 1000' and send or relay that signal (or generate and send some other signal) to the rewritable memory 1036', thereby altering the instructions stored thereon.

The pull tab 1040' includes a distal portion that is configured to extend around a majority of a structural support element, such as a status indicator 1050'. Stated differently, the pull tab 1040' may include a distal portion that is configured to extend around a majority of a cross-sectional profile of the status indicator 1050'. The distal portion of the pull tab 1040' may hold the pull tab 1040' in place until a proximal force of sufficient magnitude is applied to the pull tab 1040', thereby causing the distal portion of the pull tab 1040' to deflect laterally such that the pull tab 1040' can be displaced in a proximal direction. In other words, the pull tab 1040' (or a distal portion thereof) may be formed from material with sufficient flexibility such that the pull tab 1040' may deflect around the status indicator 1050' as the pull tab 1040' is withdrawn.

The pull tab 1040' may also include an aperture 1046' that extends through both a first (e.g., upper) surface of the pull tab and a second (e.g., lower) surface of the pull tab 1040'. The aperture 1046' is sized and shaped such that a battery may contact the battery contact 1032' through the aperture 1046' when the pull tab assembly 1000' is in the operable state depicted in FIG. 10E.

As depicted in FIGS. 10D-10G, the pull tab 1040' may also include a non-conductive solid portion that is disposed proximal and distal of the aperture 1046'. This solid portion of the pull tab 1040' is configured to disrupt electrical contact between the battery and the battery contact 1032' when the pull tab assembly 1000' is in the states depicted in FIGS. 10D and 10F.

The pull tab 1040' may also include one or more indicia 1042' that indicate the pull direction for withdrawing the pull tab 1040' from the housing 1010'. For example, in the depicted embodiment, a proximal portion of the pull tab 1040' includes a plurality of arrow-shaped cut-outs, with the tips of the arrows pointed in the pull direction. The one or more indicia 1042' may be configured to provide improved grip to the pull tab 1040'. In some embodiments, such as that depicted in FIGS. 10D-10G, such improved grip may arise as a result of indicia 1042' that are cut out of the pull tab 1040'.

The pull tab assembly 1000' is configured to transition from an initial (inoperable) state (see FIG. 10D) to a first (operable) state (see FIG. 10E), then transition from the first (operable) state (see FIG. 10E) to a second (inoperable) state (see FIG. 10F), then transition from the second (inoperable) state (see FIG. 10F) to the first (operable) state (see FIG. 10G) as the pull tab 1040' is displaced relative to the battery and the battery contact 1032'. Stated differently, as the pull tab 1040' is withdrawn from the housing 1010', the pull tab assembly 1000' first transitions from a state in which the battery is not electrical contact with the negative battery contact 1032' (see FIG. 10D) to a state in which the battery is in electrical contact with the negative battery contact 1032' (see FIG. 10E), then transitions back to a state in which the battery is not in electrical contact with the negative battery contact 1032' (see FIG. 10F), then transition back to a state in which the battery is in electrical contact with the negative battery contact 1032'. In the depicted embodiment, this transition process can be accomplished as the pull tab 1040' is withdrawn in a single direction.

Referring to the embodiment of FIGS. 10A-10C and the embodiment of FIGS. 10E-10G, the "first" state has been used to refer to an operable state and the "second" state to an inoperable state, however, various embodiments in the device is initially in an operable or inoperable state are within the scope of this disclosure. The relative positions of the negative battery contact 1032, 1032' and the aperture 1046, 1046' may be configured to transition the device between operable an inoperable states the pull tab 1040, 1040' is withdrawn, and to determine whether an initial state is operable or inoperable.

Figure 11A:
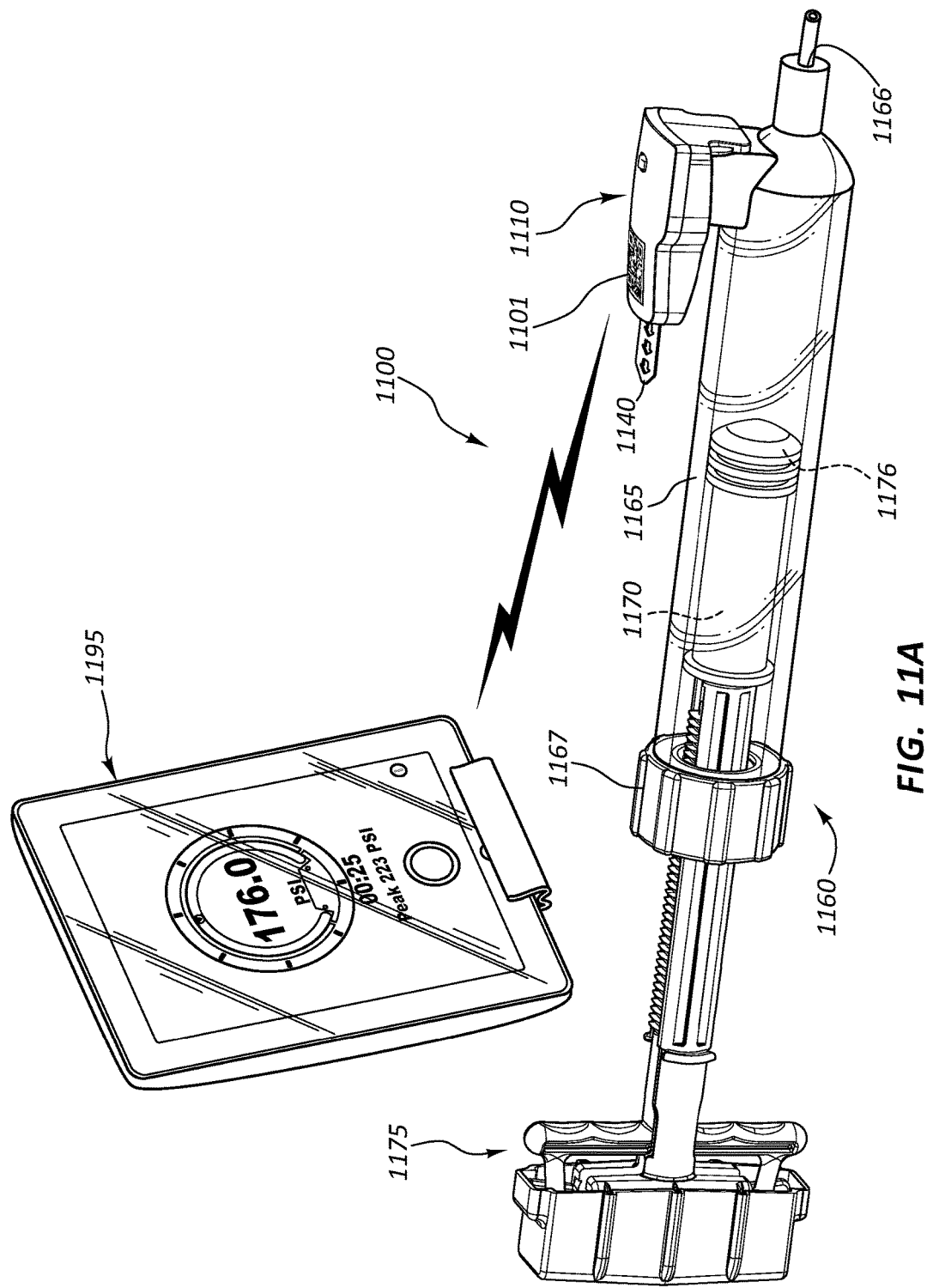
FIG. 11A is a perspective view of a pull tab assembly, according to another embodiment.
Figure 11B:
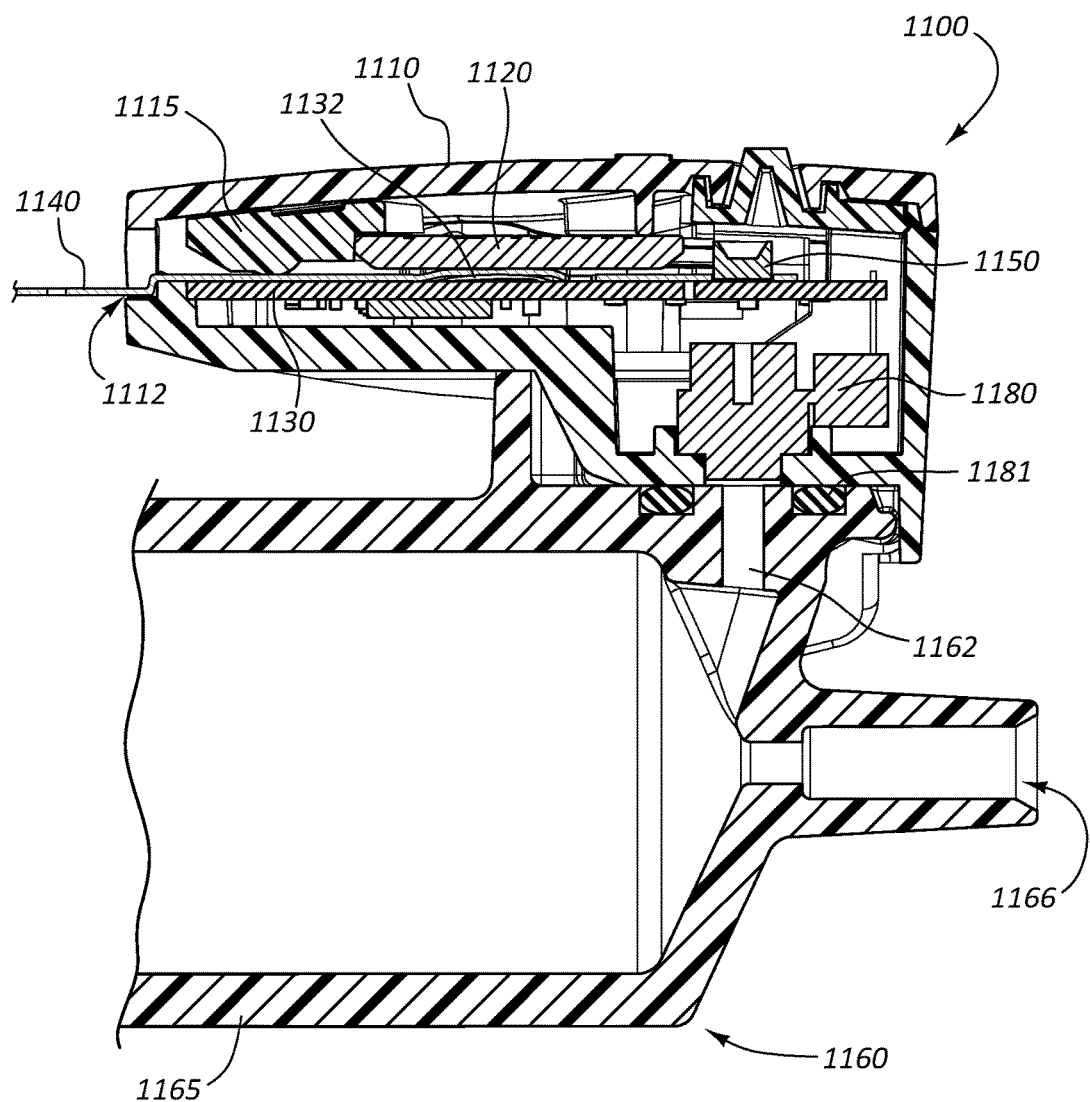
FIG. 11B is a cross-sectional side view of a portion of the pull tab assembly of FIG. 11A.

FIGS. 11A and 11B depict a pull tab assembly 1100, according to another embodiment. More particularly, FIG. 11A provides a perspective view of the pull tab assembly 1100, while FIG. 11B provides a cross-sectional side view of a portion of the pull tab assembly 1100.

The pull tab assembly 1100 includes a housing 1110, a battery 1120, a circuit board 1130, a negative battery contact 1132, a pull tab 1140, a slot 1112, a rewritable memory (not shown), and a transmitter (not shown) that are analogous to the housing 1010, battery, circuit board 1030, negative battery contact 1032, pull tab 1040, slot 1012, rewritable memory 1036 and transmitter 1090 depicted in connection with FIGS. 10A-10C. Indeed, the embodiment depicted in FIGS. 11A and 11B can be understood as including all of the features of the pull tab assembly 1000 as shown and described in connection with FIGS. 10A-10C, plus additional features described below.

Thus, as depicted in FIGS. 11A-11B, in addition to the features described in connection with pull tab assembly 1000, the pull tab assembly 1100 further includes an inflation device 1160 that is coupled to the housing 1110.

The inflation device 1160 may be coupled to the housing 1110 by any suitable manner. For example, the inflation device 1160 may couple to the housing 1110 via a snap-fit type connection. As used herein, snap-fit type connections refer very broadly to a wide variety of fits or connections, such as connections that rely on friction between component parts (as opposed to adhesive or mechanical fasteners) to couple the component parts. In some embodiments, snap-fit connections include a groove or slot in a first component, configured to receive a second component. One or more protrusions, tabs, ridges, ribs, barbs, or other locking features may be disposed such that the feature is deformed when the second component is pushed into the receiving portion of the second component. Once the second component is in place, the locking feature may return to its initial position and lock the second component in place.

A wide variety of features (e.g., protrusions, tabs, ridges, barbs, slots, channels, holes, and so on) may be configured for use in connection with a snap fit. In embodiments wherein the inflation device 1160 is configured to couple to the housing 1110 via a snap-fit type mechanism, mating features may be found on both components, or may be only identifiable on one of the two components. Still further, in some embodiments protruding-type locking elements (e.g., barbs, ridges, and so on) are on either or both components and receiving-type locking elements (e.g., grooves, slots, and so on) are on either or both components.

The inflation device 1160 includes three broad groups of components; each group may have numerous subcomponents and parts. The three broad component groups are: a body component such as syringe body 1165, a pressurization component such as plunger 1170, and a handle 1175.

The syringe body 1165 may be formed of a generally cylindrical hollow tube configured to receive the plunger 1170. The syringe body 1165 may include an inlet/outlet port 1166 located adjacent the distal end of the syringe body 1165. In some embodiments, a coupling member 1167 is coupled to the syringe body 1165 adjacent the proximal end of the syringe body 1165. The coupling member 1167 may include a center hole configured to allow the plunger 1170 to pass through the coupling member 1167 into the syringe body 1165. Further, the coupling member 1167 may include coupling member threads (not shown) configured to selectively couple the coupling member 1167 to the plunger 1170.

The plunger 1170 may be configured to be longitudinally displaceable within the syringe body 1165. The plunger 1170 may extend from the handle 1175 to a seal 1176 at the distal end of the plunger 1170.

The handle 1175 broadly refers to the group of components coupled to the proximal end of the plunger 1170, some of which may be configured to be graspable by a user. In certain embodiments, the handle 1175 is configured such that the user can manipulate the position of the plunger 1170 by manipulating the handle 1175. Further, in some embodiments, the handle 1175 includes an actuator mechanism configured to manipulate components of the inflation device 1160.

The pull tab assembly 1100 may further include a pressure sensor 1180 and a transmitter. In some embodiments, the pressure sensor 1180 and/or transmitter (not shown) are disposed within the housing 1110.

The pressure sensor 1180 may be configured to measure the pressure within the syringe body 1165. For example, FIG. 11B illustrates how a channel 1162 may provide fluid communication with the pressure sensor 1180. The pressure sensor 1180 may comprise any number of known pressure sensors. For example, the pressure sensor 1180 may be a transducer. In some embodiments, the pressure sensor 1180 measures gauge pressure, such that when pressure within the syringe body 1165 drops below atmospheric pressure, the gauge reads a negative pressure. Additionally, the pressure sensor 1180 may be sealed such that the reference pressure does not change with changes in environmental atmospheric pressure. The pressure sensor 1180 may be a force collector such as a piezoresistive strain gauge, a capacitive diaphragm, an electromagnetic diaphragm, or a potentiometric gauge.

The pressure sensor 1180 may connect to the circuit board 1130. For example, in the depicted embodiment, the pressure sensor 1180 includes one or more connection points that are configured to connect the pressure sensor 1180 to the bottom surface of the circuit board 1130.

The pressure sensor 1180 may be configured to be in direct fluid communication with the interior portion of the syringe body 1165. Thus, in some embodiments, no secondary fluid—such as a gel—is disposed between the pressure sensor 1180 and the interior portion of the syringe body 1165. A system configured for use without a gel or secondary fluid may remove the risk that inconsistencies (such as bubbles or leaks) in the secondary fluid will undesirably alter sensor measurements.

A seal, such as an O-ring 1181, may be configured to isolate the pressure sensor 1180 from the outside environment. In other words, the O-ring 1181 may be positioned such that the pressure sensor 1180 is in fluid communication with the interior portion of the syringe body 1165 but not with other areas of pressure. In the illustrated embodiment, the O-ring 1181 is configured to be disposed around the perimeter of the channel 1162 such that the O-ring 1181 seals the fluid communication between the pressure sensor 1180 and the channel 1162 when the pull tab assembly 1100 is assembled.

The transmitter (obscured by other components in FIGS. 11A and 11B) may be configured to transmit and/or receive radio waves. For example, the transmitter may be configured as a Bluetooth transmitter and/or as a Wi-Fi transmitter. One potential benefit of Bluetooth transmission is that the power consumption of the transmitter may be less than that of a Wi-Fi transmitter. The transmitter may also be configured to transmit other forms of electromagnetic radiation instead of radio waves, such as, for example, infrared light. Still further, the transmitter may be configured to transmit other waves or signals, for example, sound waves. In some embodiments, the transmitter is located on the top surface of the circuit board 1130. The transmitter may be configured to transmit pressure data when the pull tab 1140 is displaced.

The transmitter allows for wireless remote display of pressure signals generated by the pressure sensor 1180. In other words, a remote display 1195 may receive a wireless signal, such as a Bluetooth signal, from the transmitter of the pull tab assembly 1100, convert that signal into pressure data, and then transmit the pressure data via a wireless signal, such as a Wi-Fi signal, to a server (such as a cloud server) that stores patient data.

The remote display 1195 may provide significant benefits. For example, the transmitter may allow multiple individuals to be aware of the pressure conditions of a medical device used on the patient. This knowledge may in turn assist surgical staff to work as a team instead of waiting for instructions from the user of the inflation device. In some embodiments, the remote display is a portable display, such as a laptop or tablet.

The remote display 1195 may be configured such that a user can initiate a connection (for example, pair the remote display 1195 with the remaining portions of the pull tab assembly 1100 via Bluetooth) through interaction with one or both components. For example, when the remote display 1195 is not in communication with rest of the pull tab assembly 1100, the remote display 1195 may indicate that the pull tab assembly 1100 is not connected with the remote display 1195. When a user manipulates the remote display 1195 (e.g., touches a "connect" button), then the remote display 1195 may initiate an algorithm to search for wireless signals generated by the transmitter.

Alternatively, the pull tab assembly 1100 may be configured with a bar code or a QR code 1101 configured to provide connection data to the portable remote display 1195. For example, the pull tab assembly 1100 may have the bar code, the QR code 1101, or some other computer-readable information attached directly to the pull tab assembly 1100 and/or attached to packaging of the pull tab assembly 1100. The portable display device 1195 may be configured with one or more components configured to read this information. For example, the portable display device 1195 may include a camera. A user could position the camera such that it reads the bar code or QR code 1101. The bar code or QR code 1101 could directly provide information regarding connection of the pull tab assembly 1100 to the portable remote display 1195. Additionally, or alternatively, the bar code or QR code 1101 may indirectly provide information by directing the device to an internet or a network location to obtain data, and/or may provide information (e.g., operating parameters of the inflation device or a coupled medical device) other than connection information.

In some instances, the pull tab assembly 1100 may be configured with a status indicator 1150 configured to communicate the connection status of the pull tab assembly 1100. For example, the status indicator 1150 may include a light emitting diode (LED) or other light, or may include mechanical indicia, such as an arrow or other member disposed in a particular orientation when the transmitter is connected to the remote display 1195. In some instances multiple LED lights may be used. For example, the status indicator may emit red light when the device is powered but not connected and green light when the transmitter is connected with (for example, wirelessly paired with) the portable remote display 1195.

While FIGS. 11A-11B disclose a pull tab assembly that includes the inflation device 1160, other pull tab assemblies may include or be used in connection with a wide variety of instruments, toys, or other items in which selective interruption of a connection between a battery and a battery contact is desired.

Without further elaboration, it is believed that one skilled in the art can use the preceding description to utilize the present disclosure to its fullest extent. The examples and embodiments disclosed herein are to be construed as merely illustrative and exemplary, and not as a limitation of the scope of the present disclosure in any way. It will be apparent to those having skill in the art that changes may be made to the details of the above-described embodiments without departing from the underlying principles of the disclosure herein. It is intended that the scope of the invention be informed by the claims appended hereto and their equivalents.

The invention claimed is:

1. A pull tab assembly for selectively interrupting an electrical connection with a battery, the assembly comprising:
   a battery;
   a first battery contact; and
   a pull tab that is configured to selectively interrupt an electrical connection between the battery and the first battery contact,
   wherein the assembly is configured to transition from a first state to a second state and subsequently from the second state to the first state as the pull tab is displaced relative to the battery and the battery contact,
   wherein the battery is in electrical contact with the first battery contact when the assembly is in the first state, and the battery is not in electrical contact with the first battery contact when the assembly is in the second state,
   wherein the assembly is configured to transition from the first state to the second state and subsequently from the second state to the first state as the pull tab is displaced in a single direction.

2. The pull tab assembly of claim 1, wherein the assembly is configured to transition from an initial state to the first state as the pull tab is displaced relative to the battery and the battery contact;
 wherein the battery is not in electrical contact with the first battery contact when the assembly is in the initial state.

3. The pull tab assembly of claim 2, wherein the assembly is configured to transition from the initial state to the first state, from the first state to the second state, and subsequently from the second state to the first state as the pull tab is displaced in a single direction.

4. The pull tab assembly of claim 1, further comprising:
 an electronic circuit that comprises the first battery contact; and
 a housing that is configured to substantially enclose the battery and the electronic circuit, the housing comprising a first slot that permits at least partial withdrawal of the pull tab from the housing;
 wherein the assembly is configured to transition from the first state to the second state and subsequently from the second state to the first state as the pull tab is at least partially withdrawn from the housing.

5. The pull tab assembly of claim 4, wherein the electronic circuit further comprises a second battery contact, wherein the first battery contact is configured to form an electrical connection with an anode of a battery and the second battery contact is configured to form an electrical connection with a cathode of a battery.

6. The pull tab assembly of claim 4, wherein the electronic circuit further comprises a second battery contact, wherein the first battery contact is configured to form an electrical connection with a cathode of a battery and the second battery contact is configured to form an electrical connection with an anode of a battery.

7. The pull tab assembly of claim 4, wherein an entirety of the pull tab is configured to be withdrawn from the housing through the first slot.

8. The pull tab assembly of claim 4, wherein a proximal portion of the pull tab, but not a distal portion of the pull tab, is configured to be withdrawn from the housing through the first slot.

9. The pull tab assembly of claim 8, wherein
 the first slot defines a width; and
 the pull tab comprises a proximal portion having a first width and a distal portion having a second width, wherein the first width is less than the width of the first slot and the second width is greater than the width of the first slot.

10. The pull tab assembly of claim 4, wherein the pull tab comprises one or more indicia that indicate the pull direction for at least partially withdrawing the pull tab from the housing.

11. The pull tab assembly of claim 10, wherein the one or more indicia are configured to provide improved grip to the pull tab.

12. The pull tab assembly of claim 1, wherein the pull tab comprises perforations.

13. The pull tab assembly of claim 1, wherein the pull tab comprises:
 a first surface;
 a second surface disposed opposite the first surface; and
 a first aperture that extends through both the first surface and the second surface of the pull tab.

14. The pull tab assembly of 13, wherein the battery contacts the first battery contact through the first aperture when the assembly is in the first state.

* * * * *